United States Patent
Arnott

(10) Patent No.: US 10,569,045 B2
(45) Date of Patent: Feb. 25, 2020

(54) APPARATUS AND METHOD FOR MAINTAINING AIRWAY PATENCY AND PRESSURE SUPPORT VENTILATION

(71) Applicant: Richard J. Arnott, Pittsburgh, PA (US)

(72) Inventor: Richard J. Arnott, Pittsburgh, PA (US)

(*) Notice: Subject to any disclaimer, the term of this patent is extended or adjusted under 35 U.S.C. 154(b) by 21 days.

(21) Appl. No.: 15/995,190

(22) Filed: Jun. 1, 2018

(65) Prior Publication Data
US 2018/0272101 A1 Sep. 27, 2018

Related U.S. Application Data

(63) Continuation-in-part of application No. 15/140,531, filed on Apr. 28, 2016, now abandoned, which is a continuation-in-part of application No. 14/460,385, filed on Aug. 15, 2014, now abandoned, which is a continuation-in-part of application No. 14/011,845,
(Continued)

(51) Int. Cl.
| | |
|---|---|
| *A61M 16/20* | (2006.01) |
| *A61M 16/00* | (2006.01) |
| *A61M 16/08* | (2006.01) |
| *A61M 16/04* | (2006.01) |

(52) U.S. Cl.
CPC ...... *A61M 16/202* (2014.02); *A61M 16/0066* (2013.01); *A61M 16/0461* (2013.01); *A61M 16/0875* (2013.01); *A61M 16/0465* (2013.01); *A61M 2016/003* (2013.01); *A61M 2016/0036* (2013.01); *A61M 2205/0266* (2013.01); *A61M 2205/3561* (2013.01)

(58) Field of Classification Search
CPC ............ A61M 16/202; A61M 16/0461; A61M 16/0875; A61M 16/0066; A61M 2205/0266; A61M 2016/003; A61M 2016/0036; A61M 2205/3561; A61M 16/0465; A61M 16/201; A61M 16/203; A61M 16/204; A61M 16/205; A61M 2205/3337; A61M 16/20; A61M 2039/0666; A61M 39/22; A61M 2039/226; F16K 27/0218; F16K 27/042; F16K 27/041
USPC .......................... 251/129.2, 173; 137/15.25
See application file for complete search history.

(56) References Cited

U.S. PATENT DOCUMENTS

| | | |
|---|---|---|
| 4,192,152 A | 3/1980 | Armstrong et al. |
| 4,655,213 A | 4/1987 | Rapoport et al. |

(Continued)

*Primary Examiner* — Timothy A Stanis
*Assistant Examiner* — Arielle Wolff
(74) *Attorney, Agent, or Firm* — McKay & Associates, P.C.

(57) ABSTRACT

An assembly for modifying airflow into a nasopharyngeal airway of a patient. A valve assembly is adapted to attach to an airflow generator. A solenoid including a piston is mounted exterior to a feed tube. A butterfly valve is within the feed tube at the inlet. A pin is within the piston, and a shaft of the butterfly valve is bent to connect to the pin such that the solenoid can drive the butterfly valve. An exhalation valve is within the feed tube at the outlet, the exhalation valve adapted to slide axially within the feed tube and incrementally cover the outlet. Upon rotation of the butterfly valve, the exhalation valve thereby slides towards the mask side, wherein upon activation of both the airflow generator and a controller circuit, pressurized air from the airflow generator continuously enters the feed tube but is converted to a single, repeatable burst or rush.

6 Claims, 18 Drawing Sheets

Related U.S. Application Data filed on Aug. 28, 2013, now abandoned, which is a continuation-in-part of application No. 12/897,809, filed on Oct. 5, 2010, now Pat. No. 8,544,468.

(56) References Cited

U.S. PATENT DOCUMENTS

| | | | |
|---|---|---|---|
| 4,773,441 A | 9/1988 | Biba | |
| 5,148,802 A | 9/1992 | Sanders et al. | |
| 5,165,878 A | 11/1992 | Inagaki | |
| 5,257,772 A * | 11/1993 | Habicht | F16K 27/0218 251/305 |
| 5,259,373 A | 11/1993 | Gruenke et al. | |
| 5,549,106 A | 8/1996 | Gruenke et al. | |
| 5,645,054 A | 7/1997 | Cotner et al. | |
| 5,694,923 A * | 12/1997 | Hete | A61M 16/20 128/204.18 |
| 5,922,003 A * | 7/1999 | Anctil | A61B 17/32002 156/293 |
| 5,931,159 A | 8/1999 | Suzuki | |
| 6,047,718 A | 4/2000 | Konsky et al. | |
| 6,182,657 B1 * | 2/2001 | Brydon | A61M 16/0057 128/204.18 |
| 6,189,905 B1 * | 2/2001 | Yelverton | B62K 25/08 280/201 |
| 6,269,811 B1 | 8/2001 | Duff et al. | |
| 6,299,581 B1 | 10/2001 | Rapoport et al. | |
| 6,378,520 B1 * | 4/2002 | Davenport | A61M 16/00 128/204.26 |
| 6,443,154 B1 | 9/2002 | Jalde et al. | |
| 6,484,719 B1 | 11/2002 | Berthon-Jones | |
| 6,488,634 B1 | 12/2002 | Rapoport et al. | |
| 6,581,599 B1 | 6/2003 | Stenzler | |
| 8,544,468 B2 | 10/2013 | Arnott | |
| 2002/0010488 A1 | 1/2002 | Crawford | |
| 2003/0192543 A1 | 10/2003 | Arnott | |
| 2003/0198558 A1 * | 10/2003 | Nason | A61M 5/14244 417/53 |
| 2004/0016433 A1 * | 1/2004 | Estes | A61M 16/024 128/204.21 |
| 2011/0277754 A1 | 11/2011 | McKinnon et al. | |
| 2012/0085348 A1 * | 4/2012 | Chalvignac | A61M 16/20 128/204.21 |
| 2015/0059750 A1 | 3/2015 | Arnott | |
| 2016/0045705 A1 | 2/2016 | Arnott | |

* cited by examiner

FIG: 15

APPARATUS AND METHOD FOR MAINTAINING AIRWAY PATENCY AND PRESSURE SUPPORT VENTILATION

CROSS-REFERENCE TO RELATED APPLICATIONS

The instant application is a continuation-in-part of U.S. application Ser. No. 15/140,531, filed Apr. 28, 2016, which was a continuation-in-part of U.S. application Ser. No. 14/460,385, filed Aug. 15, 2014, which was a continuation-in-part of U.S. application Ser. No. 14/011,845, filed Aug. 28, 2013, now abandoned, which was a continuation-in-part of U.S. application Ser. No. 12/897,809, filed Oct. 5, 2010, now U.S. Pat. No. 8,544,468, which claimed benefit of provisional application Ser. No. 61/249,323 filed Oct. 7, 2009 and provisional application Ser. No. 61/258,257 filed Nov. 5, 2009, the disclosures of all of which are incorporated herein by reference.

BACKGROUND

Field of the Invention

The invention relates to the modification of pre-existing airflow generation means to produce a pressurized airflow burst or flow of air directed into the nasopharyngeal airway or trachea of the patient as a patient's inhalation action continues or is caused to occur.

Description of the Related Art

Breathing disorders or respiratory related problems widely exist for conditions such as sleep apnea, ventilation support, pharmaceutical delivery systems, and manual resuscitation. A new study suggests that CPAP therapy reduces nightmares in veterans with post-traumatic stress disorder (PTSD) and obstructive sleep apnea (OSA), and CPAP machines could indeed become an alternative treatment for those with asthma. Each of these conditions requires a system, method and apparatus for treatment. Several of these markets are sustained today by a related line of products each having one thing in common, namely pressurized ventilation support referred to as Positive Airway Pressure (PAP). In most cases conditions are treated by a continuous positive pressure air source or a continuous positive pressure gas source. At times there may be variations such as a bi-level positive pressure air or gas source delivered by a self-contained product for comfort. Unfortunately, there are several circumstances where a continuous positive pressure air or gas source is not comfortable, reasonable or useful and a standard bi-level product is cost prohibitive.

In the case of Obstructive Sleep Apnea or OSA, the gold standard remains to be a continuous positive pressure of air, which is uncomfortable to say the least. Many patients cannot tolerate the application of continuous positive airway pressure, particularly because of the discomfort associated with exhalation against a continuous positive pressure or the dryness that accompanies this type of delivery. A solution has been developed to alleviate this problem by the addition of a method and apparatus, to an existing continuous positive pressure of air, which converts a substantially constant elevated airway pressure to the patient's airway, with periodic short term reductions of the elevated airway pressure to a pressure of lesser magnitude. A further advance in such treatment involves the application of alternative high and low-level positive airway pressure wherein the low-level pressure coincides with the breath exhalation of the patient's breathing cycle.

Although more expensive devices may be available that provide relief upon exhalation, they are cost-prohibitive, designed for a single use and tightly regulated by insurance companies. In some cases no device is available at all. By providing a limited reuse/disposable add on or in some cases a durable add on regulating device, the cost, hygiene and comfort for these patients become palatable.

In addition, when different drugs, including oxygen, are delivered to a patient via continuous pressure the drug amount is difficult to regulate because breathing rates differ from patient to patient. Take the case of a comatose or mentally handicapped patient. Coordinating inhalation of drug delivery with the breathing cycle is impossible. Yet, with a bi-level attachment to oxygen or a continuous air delivery system, an appropriate treatment amount is delivered and waste is minimized.

There are several bi-level apparatus devices available. Each has a specific use and is self-contained. Some are manually manipulated. However, there is no method or device that can be added to an existing continuous positive air or gas source which will convert them for the application and delivery of bi-level positive airway pressure to a patient.

The systems, methods and apparatus disclosed in the prior art for treating patients afflicted with such maladies as sleep apnea, snoring, ventilation support and pharmaceutical delivery present a number of problems which need to be addressed. The equipment utilized in such treatment is far too limiting. In the case of sleep apnea, the air stream delivered to the patient tends to dehydrate the nasopharyngeal tissue. The unnatural sensation and discomfort experienced by the patient in overcoming the positive pressure during exhalation results in many patients abandoning the use of a system that is in all other respects quite beneficial. An alternative, much more expensive device is rejected by many insurance companies. By supplying a device as a simple add-on product it is possible to convert these devices to a comfortable useful source of treatment, as follows.

SUMMARY

It is the objective of the instant invention to provide a device which may be added to any continuous positive air pressure (CPAP) or gas source be it in the home, hospital or via emergency medical treatment.

It is further the objective of the invention to lessen the unnatural sensation and discomfort experienced by the patient in overcoming the traditional positive pressure during breath exhalation.

It is further the objective of the invention to supply the device as a simple add-on product to convert these traditional CPAP units to a useful source of treatment without considerable expense.

Accordingly, what is provided is an assembly for modifying airflow into a nasopharyngeal airway or trachea of a patient, comprising a valve assembly adapted to attach to an airflow generator, wherein the airflow generator is a continuous blower of a type producing a constant head of pressurized air, the valve assembly having an airflow side and a mask side, an inlet and an outlet defined between the airflow side and the mask side, and a feed tube, the valve assembly further comprising a linear actuator signaled by the airflow mounted exterior to the feed tube; an inhalation valve within the feed tube at the inlet, the inhalation valve adapted to slide axially within the feed tube and incrementally cover the inlet; an exhalation valve within the feed tube at the outlet, the exhalation valve adapted to slide axially within the feed tube and incrementally cover the outlet, a drive means for operating the inhalation valve and the exhalation valve simultaneously such that upon sliding of the inhalation valve toward the mask side, the exhalation valve thereby slides towards the mask side; a controller circuit connecting to the motor means for operating the motor means incrementally; and, wherein upon activation of both the airflow generator and the controller circuit, pressurized air from the airflow generator continuously enters the feed tube from the inlet but passes out of the outlet only when the linear actuator causes the inhalation valve to move in response to inhalation and thereby simultaneously move the exhalation valve to at least partially block the outlet such that the pressurized air is converted into a single, repeatable burst.

In one embodiment the drive means further comprises a first drive rod having a first distal end and a first proximal end, the first distal end connected to the piston on the airflow side, the first proximal end connected to the inhalation valve; and, a second drive rod having a second distal end and second proximal end, the second proximal end mounted to the piston on the mask side, the second distal end connected to the exhalation valve.

In the preferred embodiment the inhalation valve is a sliding seal valve or a butterfly valve working across the inlet.

BRIEF DESCRIPTION OF THE DRAWINGS

FIG. 17a shows a side view in vertical cross-section of the embodiment of FIG. 17.

DETAILED DESCRIPTION OF THE PREFERRED EMBODIMENTS

Figure 1:
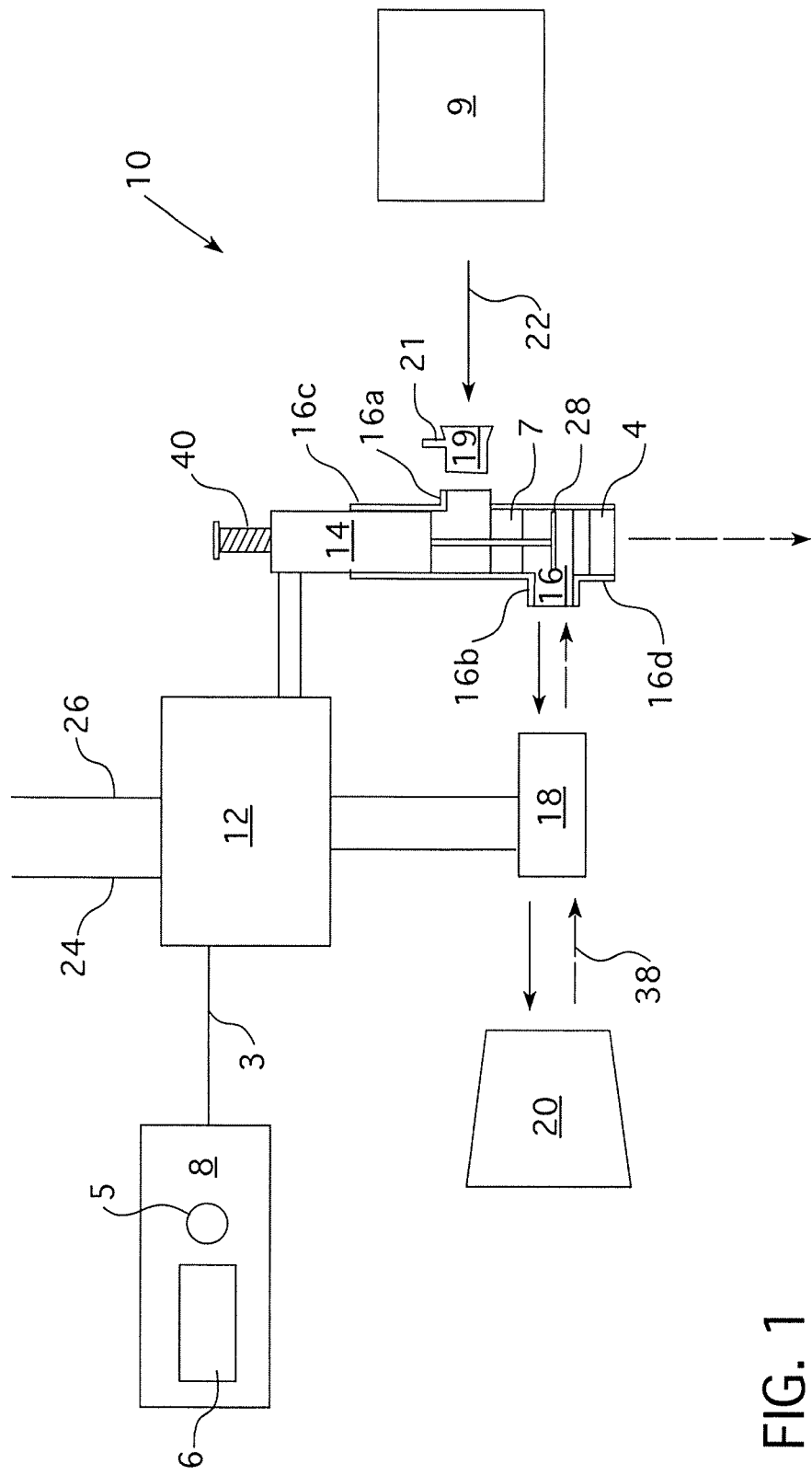
FIG. 1 shows a schematic representation and partial elevational view of the instant invention.

The invention will now be described in detail in relation to a preferred embodiment and implementation thereof which is exemplary in nature and descriptively specific as disclosed. As is customary, it will be understood that no limitation of the scope of the invention is thereby intended. The invention encompasses such alterations and further modifications and applications as would normally occur to persons skilled in the art to which the invention relates. This detailed description of this invention is not meant to limit the invention, but is meant to provide a detailed disclosure of the best mode of practicing the invention.

With reference then to FIGS. 1-6, illustrated is an assembly 10 which includes valve assembly 16, a programmable controller circuit 12 encoded by programmer 8, a normally-open electrical switch/sensor 18, and a patient interface device 20 such as a mask, tracheal tube, nasal cannula or similar patient interface, and an optional drug delivery port 19.

Valve assembly 16 has two ends 16c, 16d, an inlet 16a, an outlet 16b, and an interior feed tube 7. Valve assembly 16 further includes an electromagnetic solenoid 14 typically disposed proximate end 16c, opposite exit tube 4, which is defined at end 16d. Instead of a solenoid 14 any type of motor means may be implemented such a stepping motor. Motor means as used herein therefore encompasses any type of motor, but preferably a solenoid 14.

The airflow generator 9, which is separate from and later attached to the device, may be in the form of a blower or fan of the type used to produce a pressurized airflow, hospital wall air or compressed bottled air or gas. Airflow generator or airflow generator means therefore is used herein to define any type of blower, fan, hospital wall air, compressed air, or any traditional positive airway pressure (PAP) device, including oxygen, already attached to the same. The solid line arrows mark the air stream flow path, beginning with air drawn into the apparatus from the airflow generator 9 as indicated by arrow 22.

The electric current to operate the apparatus is supplied through conductors 24 and 26, which also supply current to solenoid 14 and switch 18. The airflow generator 9 is intended to operate continuously whereby a constant head of pressurized air is maintained. However, the solenoid 14 is at rest and will permit full air passage there through to the valve assembly 16 only when the solenoid 14 is charged by switch 18.

The valve assembly 16 of FIG. 1 further includes a flexible or rigid valve seal 28 such as a circular disc, ball or joined split ball, with the flexible valve mounted to the plunger rod 11 of solenoid 14 plunger rod 11. In alternate, the use of a slotted tube within two additional separated tubes may act as a valve (not shown). Valve seal 28 is preferably seated within the interior feed tube 7 and is operable by solenoid 14, adapted to cycle within the feed tube 7 between solenoid 14 and exit tube 4, across outlet 16b. Valve seal 28 can alternatively be placed directly within exit tube 4, which would place valve seal 28 more proximate to end 16c, so use of "within feed tube 7" is meant to encompass any location throughout the interior of valve assembly 16 since exit tube 7 is formed within the interior of valve assembly 16. In its relaxed position (shown), the valve seal 28 will at least partially cover and seal the outlet 16b or aperture of the therapy airflow or end 16d of the exit tube. The valve seal 28, in this case, is a member which normally seals against the inside surface of the feed tube 7 but will open in response to airflow passing the switch (an attempt to inhale) which signals solenoid 14 to charge (not shown) and seal against the exit tube 4 which allows the airflow to pass through the valve arrangement out of outlet 16b, the switch and thence into the patient via a patient interface device 20. "Member" as used herein can mean any shape, e.g. circular, square, etc. depending on the inside surface of the feed tube 7 as long as the seal closes against the feed tube 7.

It should be noted that the patient interface 20 and valve assembly 16 will allow unassisted inhalation and exhalation by the patient to permit entry of ambient air when the valve is in the "at rest" position. The patient interface 20 is meant to be worn in sealed relation to a patient whereby ambient air during inhalation will pass into the patient interface past valve seal 28. Exhaled breath will pass through switch 18 whereby the breath flow will be in the direction of the dotted line arrow 38, and into the valve assembly 16. Exhaled breath pressure entering the valve assembly 16 passes by the valve seal 28 which is now closed and seated against the feed tube 7, and through exit tube 4 to ambient. A return spring 40 allows the solenoid plunger rod 11 to return to its original position upstream from said outlet 16b (towards inlet 16a). This return action of the solenoid sets the switch internally whereby, as the solenoid 14 relaxes, the valve seal 28 will return back to its original position and at the same time close off the release of pressurized air or gas to complete the electrical circuit to the solenoid 14. The solenoid 14 is thereby caused to cycle open and then re-close after having permitted a "burst" of pressurized air to move into the valve assembly 16 and past the valve seal 28 out of outlet 16b and past the switch 18 and into the patient interface 20. The pressurized airflow burst is directed into the nasopharyngeal airway or trachea of the patient as the patient's inhalation action occurs, and ambient air moves through valve 16 to allow the patient to complete the breath intake voluntarily. The subsequent exhalation by the patient repeats the described process whereby a pulse, burst of pressurized air is delivered to the patient interface 20 and thence to the patient's airway as a function of each breathing cycle. An additional feature triggers the pressurized gas flow by way of an adjustable timing device should the patient not attempt to inhale himself. It should be understood that "burst" used herein and in the claims refers to a burst or flow of air of any duration and degree. For example, the produced burst can emulate that of an MPAP, or Metered Positive Airway Pressure device, wherein the burst terminates and slowly dissipates in pressure. The burst can also emulate that of a bi-level design wherein the burst has two levels of constant pressure, namely a higher level of constant therapeutic pressure upon inhalation along with a constant lower level of therapeutic pressure upon exhalation.

The pressurized airflow burst is adjustable by way of the controller circuit 12 which is encoded by way of the programmer 8. The adjustments include, but are not limited to, ramp up time, length of burst, sensitivity of the switch/sensor, timed release of burst or any combination of these settings, should they be required. The programmer 8 is linked to the control circuit by way of a cable 3 which is rigidly connected to the programmer 8 but which is detachable from the control circuit 12. Once the preferred settings have been programmed into the control circuit they will remain fixed until changed by reconnecting the programming box 8 and the settings are adjusted to alternate values. The values appear on a viewing screen 6 and are set via a navigation button 5. An additional embodiment allows the programmer 8 and control circuit 12 to be combined into a single enclosure or with cable 3 rigidly connected to both the program box and the control circuit 12 for hospital use, EMS use, testing, etc. The assembly 10 is attached to a traditional CPAP unit or traditional constant airflow generator 9 as above, which will convert that traditional CPAP unit or traditional airflow generator into a device providing an intermittent and adjustable air stream (gas), into a therapeutic burst, puff, bolus or flow of air to a patient during inhalation. By this means the patient is able to receive an air supply or concentration of gas or powdered drug, given as a single, but repeatable dose to achieve an immediate effect in transit through assembly 10 and by way of patient interface 20. The system and method thus can be utilized with pre-existing airflow generation means already implemented in homes, centers and hospitals, thereby varying the traditional constant airflow with use of the instant accessory. An assisted burst of gas given during inhalation or inspiration at the beginning of each breath will prevent collapse or maintain the upper airway, reduce inspiratory WOB (work of breathing), reduce expiratory WOB and reduce or prevent the dryness related to continuous positive airway pressure. The assisted burst itself raises the concentration in the body to a therapeutic level while allowing comfort to the patient. This is accomplished to allow the patient to finish inspiration himself and to exhale against little or no therapeutic pressure. The bolus provided is adjustable and tapers off over a period of time during the inspiration cycle, thus allowing it to maintain positive pressure throughout most of the inhalation process which will promote gas exchange in the alveoli and also keep open smaller airways. A certain amount of natural resistance experienced upon exhale through the exhalation circuit. There may be times when a greater or therapeutic pressure upon exhale is desired or required, the use of devices such as a positive end-expiratory pressure (PEEP) valve may be added to tube 4 or by the addition of a similar restrictive device being incorporated or added into the breathing circuit. As above, should it be desirable, a continuous therapeutic flow of positive pressure air upon inhalation along with a lower level of therapeutic positive pressure airflow during exhalation could result.

In some cases additional medication is required. The installation of the optional drug delivery port 19 allows the introduction of inhalable medication. Because of the assembly 10 configuration, the delivery port can be added instantly without harm to the patient or alternatively it can be applied initially and with the entry port 21 being capped until needed.

As opposed to CPAP or continuous ventilation this method allows an infinite control of therapeutic air, powdered drug or gas flow during non invasive ventilation which is critical, especially in neonates. Assembly 10 provides the clinician a means of providing safety and comfort for those who cannot speak for themselves.

Although FIG. 1 broadly illustrates the underlying system and method of the present invention, the use of different valves, sensors and components are possible. In lieu of solenoid 14 a stepping motor or similar control (not shown) may be used to control the pressurized air/gas delivery by rotating a seal within assembly 10. However, additional components similar to those shown in FIG. 2 would be required.

Figure 2:
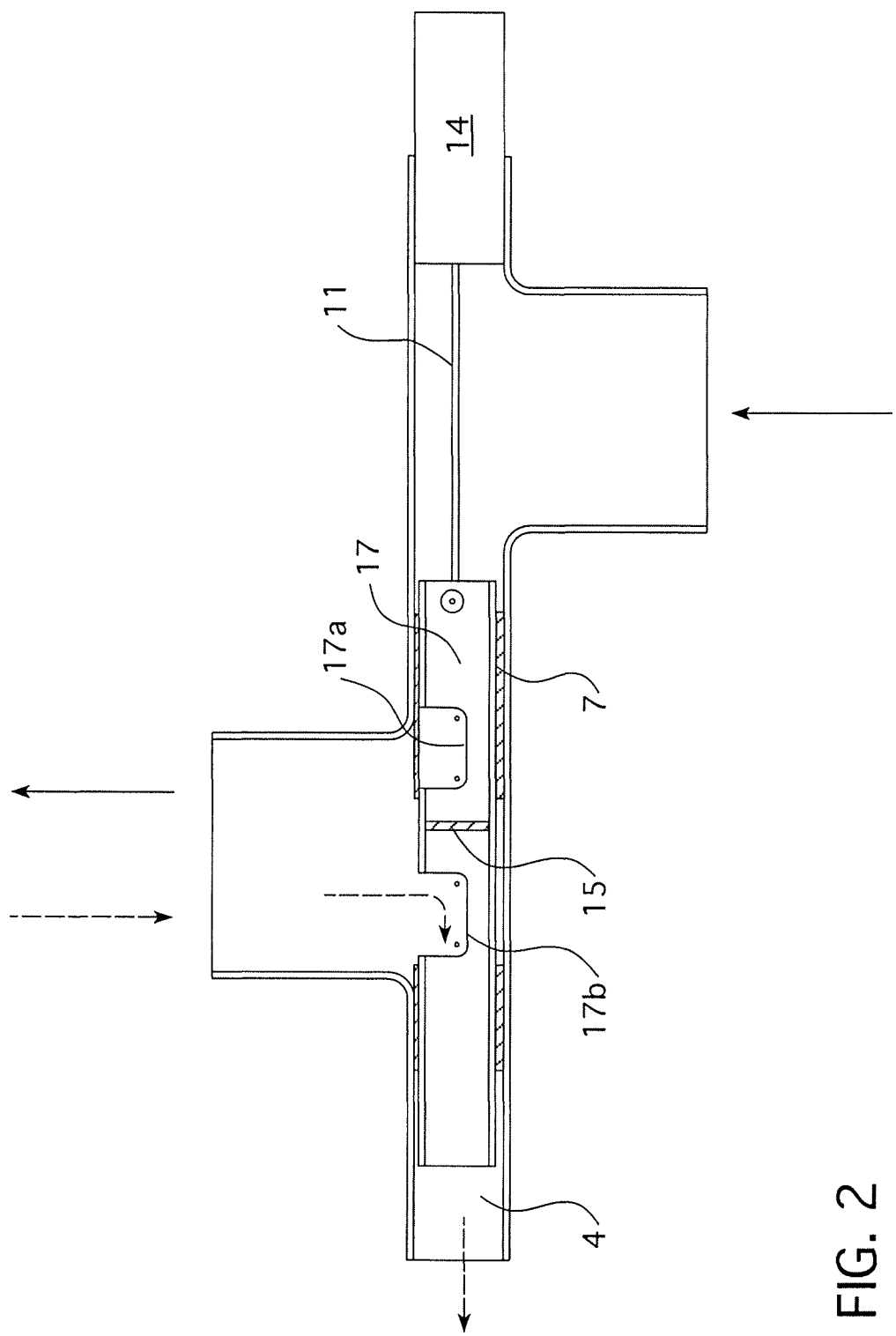
FIG. 2 shows an elevational view in partial section illustrating an alternative embodiment of the valve of the present invention.

FIG. 2 shows a sliding tube valve seal 17, whereby it replaces the above mentioned valve seal 28 with a slotted, hollow tube. The sliding tube valve seal 17 is connected to the solenoid valve 14 by way of plunger rod 11 and closes off air pressure when the solenoid 14 is relaxed as shown. At least one slot 17a is defined within the outer shell of the hollow tube. A seal or wall 15 positioned beyond slot 17a and within the sliding tube valve seal 17 directs the flow of air to the patient when the tube is pushed forward by the solenoid valve. In addition, the sliding tube valve seal 17 directs the flow of exhaled air from the patient through exit tube 4 to atmosphere. An additional hole or exhalation slot 17b or other means to allow the exhaled air to re-enter the hollow tube and proceed to exit tube 4 is defined on the other side of wall 15. The placement of the slots 17a, 17b in the tube may be adjustable or fixed in order to control both the inhalation and exhalation pressures. The sliding tube valve seal 17 slides freely within the feed tube 7 and exit tube 4 and is controlled by way of the solenoid 14.

In alternate, a second method and device for converting a constant airflow generator to a multi-level therapeutic device by way of assembly 10 attached to a CPAP unit or traditional constant airflow generator, 12 will convert a traditional CPAP unit or traditional airflow generator into a device providing an adjustable air stream, powder or gas, into multiple pressurized therapeutic air flows and delivering them to a patient.

The device is able to deliver bi-level or multiple levels of therapeutic flows of air, air powder or gas to a patient. A patient may receive one or more levels of pressurized air upon inhalation and one or more lower levels of pressurized air upon exhalation. This may be accomplished in several ways such as by leaving valve 28 open or partially open at all times and regulating the distance between valve 28 and feed tube 7 during inhalation. Thus one or more elevated pressures is delivered to patient through assembly valve 16, switch 18 and patient interface 20 upon inhalation while bleeding off the excess air and pressure through tube 4. The valve 28 would then partially adjust to a predetermined position or predetermined positions for exhale creating a lower exhalation pressure or multiple lower exhalation pressures. This could allow a bleed off of air by way of tube 4. Although not necessary, for a split second valve 28 could close against feed tube 7 and start the cycle over or the-add on device could just switch back to the higher level upon inhalation.

As a third method and device, seal 28 could close off or partially close off against tube 4 during inhalation and then open the exit port for exhalation to release a predetermined amount of air flow and pressurized air to cause the required pressure drop. The process would then repeat itself as described previously.

Figure 3:
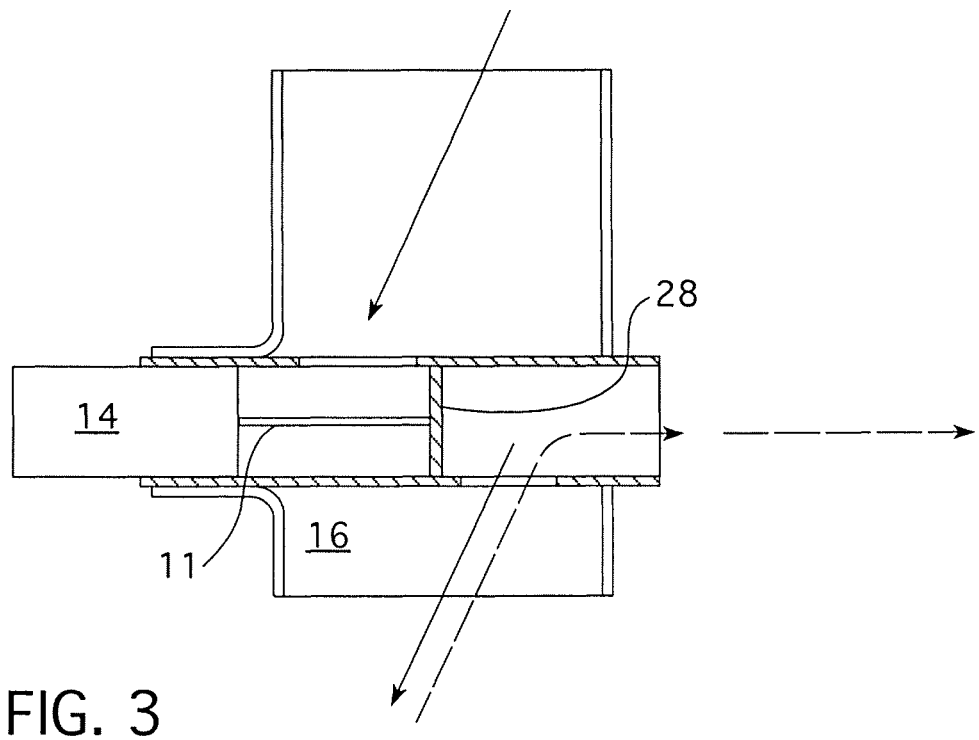
FIGS. 3 and 4 show elevational views in vertical section illustrating further embodiments of the apparatus valve of the present invention.
Figure 4:
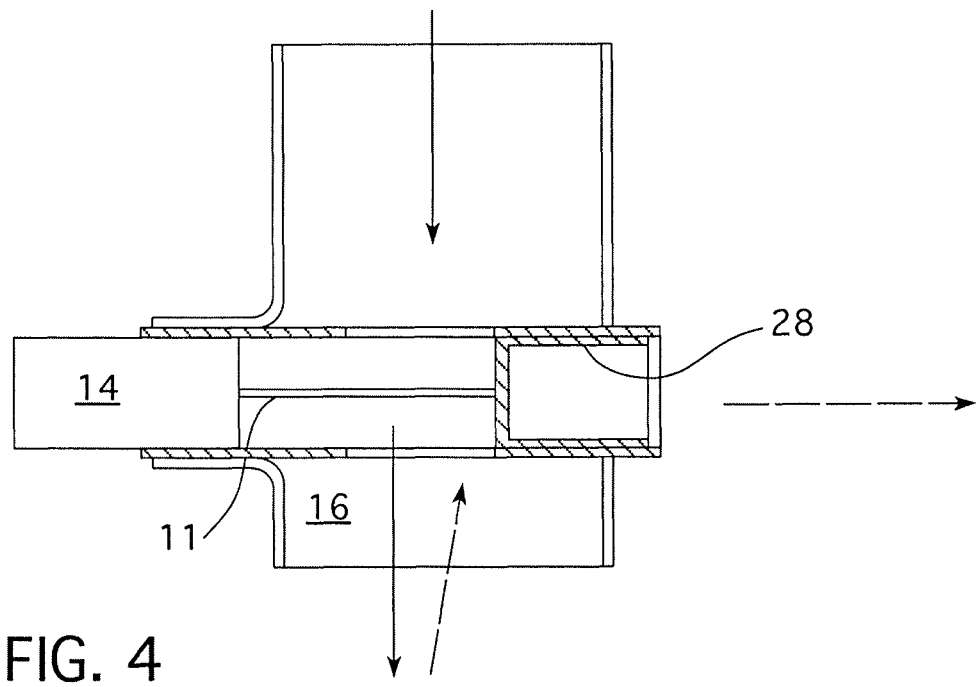

FIG. 3 and FIG. 4 illustrate smaller versions of the assembly 16 in that the airflow is controlled in a straight tube and components are more compact.

Figure 5:
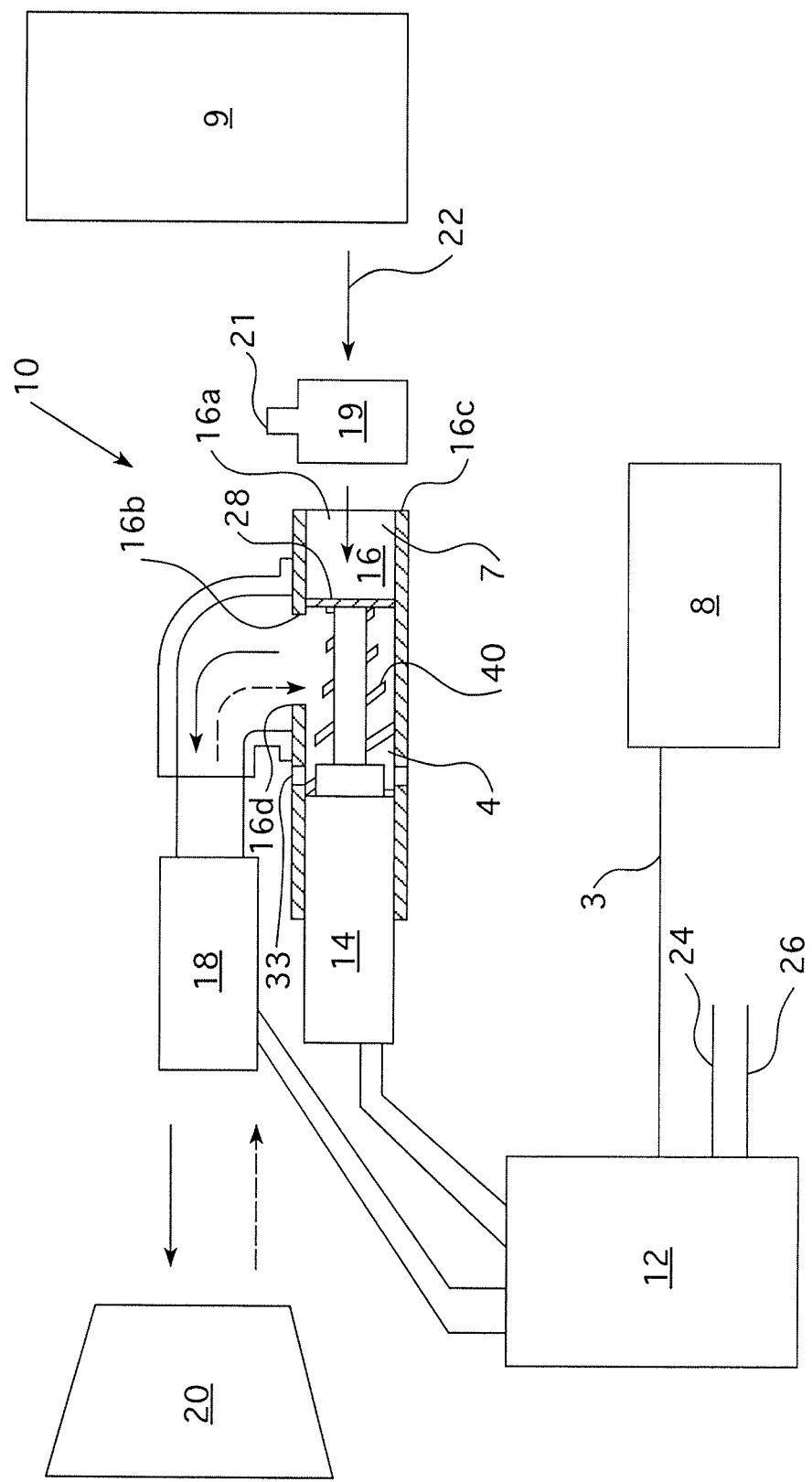
FIG. 5 shows an elevational view in vertical section illustrating still another alternative form of the system.
Figure 6:
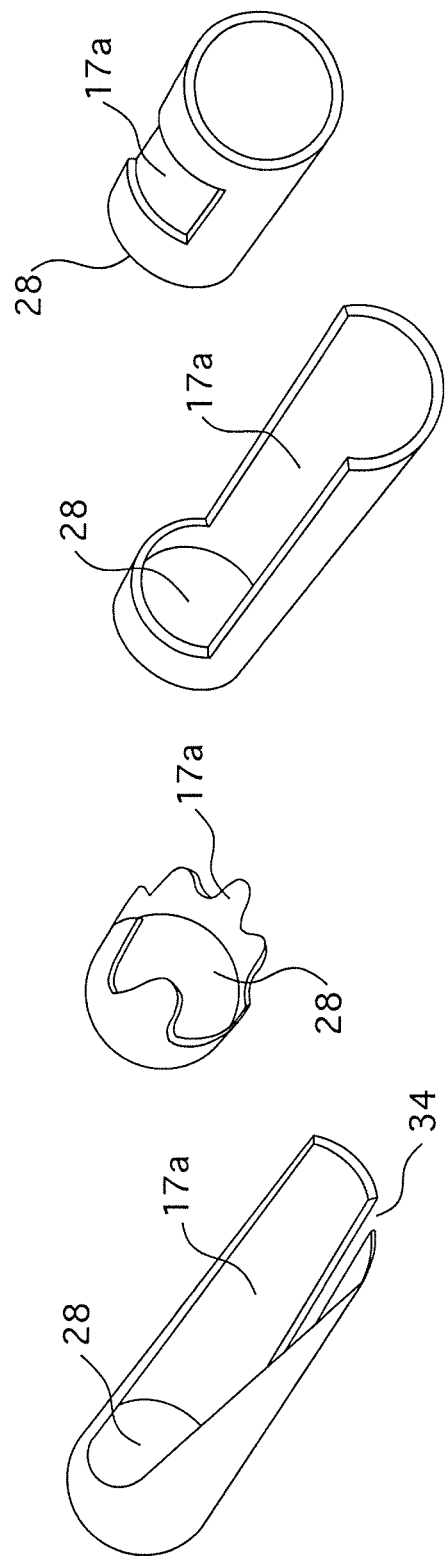
FIG. 6 shows perspective views of certain components intended for other valve embodiments.

FIG. 5 shows a fourth method and device wherein the return spring 40 may be positioned between the solenoid 14 and valve seal 28 and will be of sufficient strength to control the flow of air or gas coming from the constant air flow generator. In this embodiment the spring is compressed when the solenoid 14 is charged allowing the air flow and pressure to increase to a therapeutic level. When the solenoid 14 is at rest the air flow is restricted to a lower level or may be shut off completely. Ventilation holes 33 or slots, allow exhalation of the patient and provide ambient air should a power failure occur. In addition, these ventilation holes 33 may be restricted or sealed in order to regulate inhalation and/or exhalation pressure. As an alternate, (not shown) the return spring may be positioned within the solenoid itself between the back end of the solenoid and the tip of the plunger 11. Accordingly, "attached to" as used in relation to the spring and solenoid means the spring can be attached to the exterior of the solenoid or be integrated within the solenoid. As previously stated seal 28 could close off or partially close off against tube 4 during inhalation and then increase open the exit port for exhalation to release a predetermined amount of air flow and pressurized air to cause the required pressure drop. The process would then repeat itself as described previously.

In any of the apparatuses and methods above, the use of sliding tube valve seal 17 (slotted tube of FIG. 2) in place of the seal 28 is possible. Furthermore, with reference to FIG. 6, several controlling configurations as shown may be used in place of the sliding tube valve seal 17 in FIG. 2 or in place of valve seal 28 on FIG. 5. Any of the valve seals can be keyed by use of a slot 34 and guide. The guide may be a pin, key, roller or any variation of these. Accordingly, "tube valve seal" as defined herein means any shape of tube shown and described above and by the alternative embodiments of FIG. 6 and their obvious variations, the critical feature of which require some form of wall 28 or solid end to act as a seal and a defined slot 17a (FIG. 2) or opening to allow airflow to pass out of the tube valve seal. As in the first method the valve seal 28 can be a circular soft or rigid member which normally seals against the inside surface of the feed tube 7 on FIG. 5. The seal mates against or close to the face of a now split or two piece tube (not shown) but will respond to airflow passing the switch (an attempt to inhale) which signals solenoid 31 to charge (not shown) which allows the airflow to pass through the valve arrangement out of outlet 16b, the switch 18 and thence into the patient via a patient interface device 20. In alternate, solenoid 14 may also be made to respond to exhalation when continuous airflow during inhalation is present. In such a case valve 28 is will regulate the airflow in relation to exit tube 4.

Figure 7:
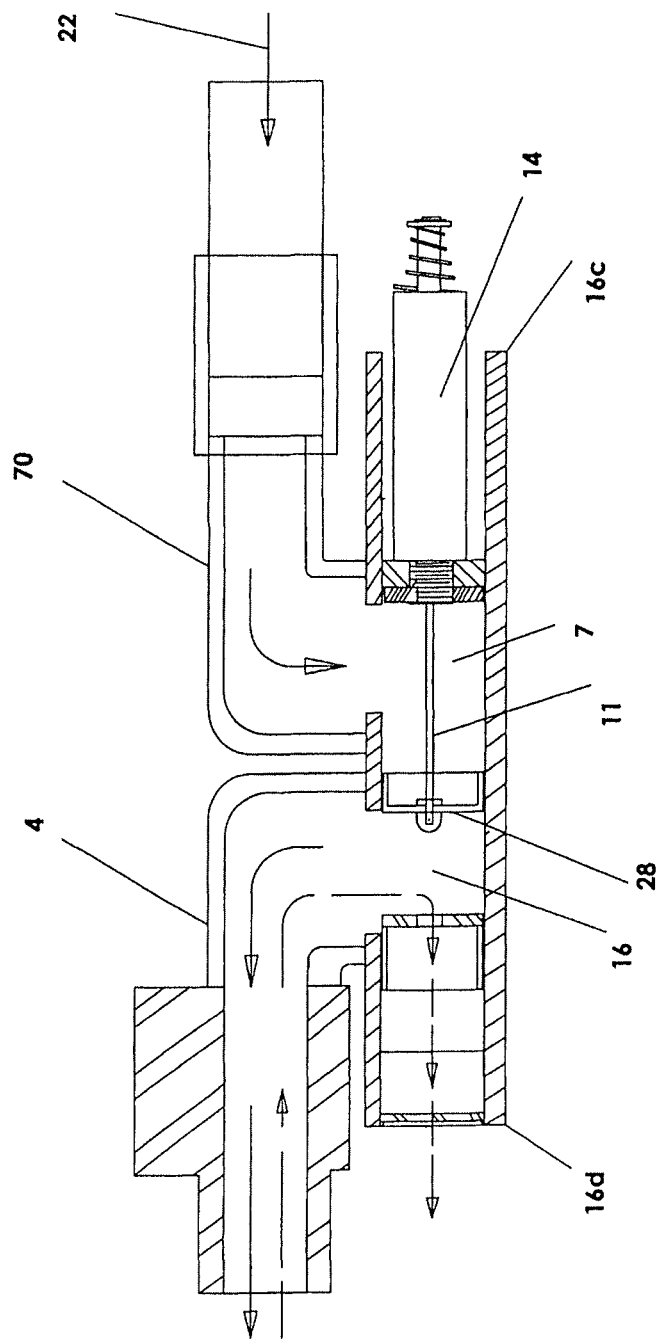
FIG. 7 shows an elevational view in vertical section illustrating a valve assembly in which a parallel tube is utilized for exiting exhalation air.

In the above embodiments it can be seen that the valve assembly 16 can take on various shapes, depending on the type of housing (not shown), valve seal 28, and other characteristics. In one embodiment, and as shown by FIG. 7, the air flow 22 can be allowed to make right turns into an exit tube 4 which is parallel to feed tube 7. Such may be desirable for generally rectangular housing shapes, and an open fiber type muffler material can be placed near the end of the valve seal 28 if desirable. Here, the motor means or solenoid 14 is still disposed at or near the proximal end 16c of the valve assembly 16 but the valve seal 28 and solenoid 14 both are situated underlying the exit tube 4 and entry chamber 70. In this embodiment the outlet is formed as exit tube 4 and inlet is formed as entry chamber 70. Namely, shown is valve assembly 16 including solenoid 14 and valve seal 28 within feed tube 7 underlying both an entry chamber 70 near the proximal end 16c and the exit tube 4 (outlet) near the distal end 16d to form the assembly generally as being U-shaped. "Underlying" therefore means the feed tube 7 containing therein the solenoid 14 is not in line with the center axes of the exit tube 4 (outlet) and entry chamber 70 (inlet).

Figure 8:
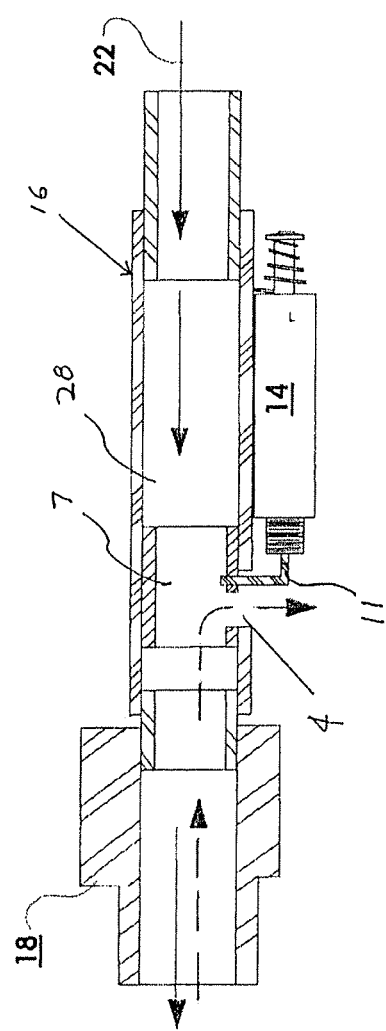
FIG. 8 shows an elevational view in vertical section illustrating a valve assembly in which a single, straight tube is utilized for both inhalation and exhalation such that the motor means for controlling the valve seal is external to the tube.
Figure 9:
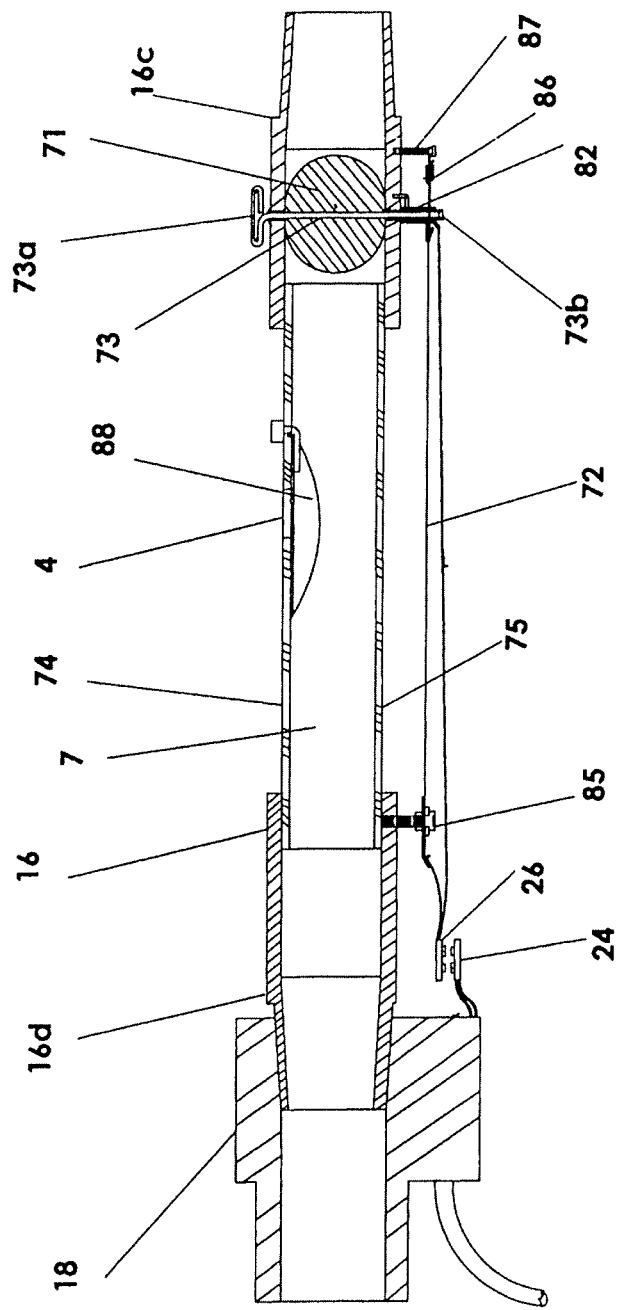
FIG. 9 shows an elevational view in vertical section of an alternative embodiment of a valve assembly in closed position and the butterfly valve in an open position allowing pressurized air to advance to the patient, and wherein the motor means excludes a solenoid and alternatively takes the form of Nitinol wire.

In the above embodiments the "motor means" includes some type of mechanical motor, e.g. a solenoid. The solenoid 14 can be placed at various locations. As shown in the above embodiments the solenoid 14 is at the end of the valve assembly 16 but inside the valve assembly 16 feed tube 7. In an alternative embodiment and as shown by FIG. 8, it is possible to place the solenoid 14 outside the feed tube 7. Omitted then are in-line exit tubes and entry chambers, wherein outlet 4 is the exit defined as a hole. Whereas above an in-line piston or in-line plunger rod 11 is attached to the solenoid 14 in a U-shaped fashion when combined with the tubing, shown by FIG. 8 is a "straight-through" design of the valve assembly 16. In order to accomplish this the solenoid 14 is moved outside the tubing or feed tube 7. Generally then the solenoid 14 is outside of the air circuit. The plunger rod 11 is still used as a sliding piston or valve on the solenoid 14 but the solenoid 14 is disposed outside of the straight tubing with the valve seal 28 extending upward from the solenoid 14. The plunger rod 11 extends upward perpendicularly from the motor means then bends to align with the motor means such the valve seal 28 moves above the motor means in alignment with the feed tube 7 such that it can still be situated to move laterally within the tubing. The straight-through design enhances pressure control, requires fewer parts, is easier to assemble, easier to clean and more cost-effective to manufacture.

In the above embodiments the valve seal and tube valve seal move laterally within or against the feed tube (or the exit tube). It should be understood that another seal embodiment may be a butterfly valve intended to accomplish the same results, however in this embodiment the valve would move an approximate quarter-turn rotationally. Therefore, in either instance of the valve seal, tube valve seal, or butterfly valve, as used in the claims, the valve will cycle back and forth in relation to the outlet and exit tube and "cycle" either laterally or rotationally.

FIGS. 9-16 show rotational sealing using a butterfly valve 71 as the valve seal. Additionally, in the aforementioned embodiments, although the tube arrangement and motor placement can vary as shown, the "motor means" continues to include some type of mechanical motor, e.g. a solenoid. Shown with continued reference to FIGS. 9-15 is an embodiment using a wire 72 and shaft 73 to move the rotational butterfly valve 71.

Specifically, shown is a valve assembly 16 including a valve seal formed as a butterfly valve 71. Since the function is equivalent to that disclosed herein, butterfly valve 71 conforms to inside of interior feed tube 7 and partially opens during inhalation and then returns to its original resting for exhalation. The process would then repeat itself as described previously. The herein disclosed controller circuits 12 (FIG. 1) and switches 18 (FIG. 1) are similarly used for this embodiment, the connections and other differences as follows.

Butterfly valve 71 is disposed proximate to one proximal end 16c of a single feed tube 7 within a valve assembly 16 adapted to attach to an airflow generator 9 (FIG. 1). Proximal end 16c is end of tube 7 which is most opposite the point of entry of exhaled patient breath. Therefore, distal end 16d is the end of tube 7 nearest the mouthpiece, hence, farthest from source of generated airflow.

Butterfly valve 71 is attached a pivot shaft 73. Shaft 73 is a perpendicular rod relative to feed tube disposed through the butterfly valve 71 along the center axis of rotation having a top shaft end 73a and bottom shaft end 73b. Top shaft end 73a terminates exterior to the top 74 of the tube 7 and bottom shaft end 73b terminates exterior to the bottom 75 of the tube 7 to anchor and maintain the butterfly valve 71 in a rotationally fixed position within the tube 7 (top and bottom used for differentiation only as the orientation of the tube may vary).

In one embodiment, attached to bottom shaft end 73b is a clutch 82. The exact structural form of the clutch 82 can vary, such as by using a clutch 82 of the wrap spring type or cam type. The clutch 82 can be as simple as a single wrap of the wire around the bottom shaft end 73b or in alternative is a direct drive through the use of a lever/tension spring combination or a cam, idler roller or floating gear train on a lever perpendicular to the shaft 73. The clutch 82 may also include an elastic band 80 (FIG. 13) or clutch spring 81 at the top shaft end 73a (FIG. 12) or secondary torsion spring 82a (FIG. 14) as a means for urging the butterfly valve 71 to its originally closed position depending on the type of clutch 82 used, the elastic band 80 or clutch spring 81 having one end connected to the top shaft end 73a as shown or being wrapped thereon.

In this continued embodiment, instead of an actual solenoid, butterfly valve 71 opens and closes using the combination of the clutch 82 and one or more nickel titanium wires 72, i.e. the metal alloy of nickel and titanium commonly known as Nitinol 72. Due to its shape-memory characteristics, the Nitinol 72 acts as a "motor" by contracting with voltage, and it can then relax or be stretched using a return spring 86 or other means. As before, the electric current to operate the apparatus is supplied through wires (only one shown) to conductors 24 and 26, which also supplies current to the Nitinol 72 and switch 18 (FIG. 1 also). Recall the airflow generator 9 is intended to operate continuously whereby a constant head of pressurized air is maintained. When the Nitinol 72 is in an un-contracted, resting state, air passage through the tube 7 is halted or restricted, and state change occurs only when the Nitinol 72 is charged by switch 18 and contracts, as follows.

Bottom shaft end 73b of shaft 73 forms a segment around which is disposed a torsion spring 82, also known as a wrap spring clutch. It should be understood that the bottom shaft end 73b may or may not include the torsion spring 82 depending on the type of clutch used, so the Nitinol in "conductive communication" with the shaft means with or without a clutch. The Nitinol may be wedged between two cams, one attached to the main shaft and one attached to a side arm. Other possible clutch types include Idler rollers or floating gears with sway arms. In the preferred embodiment, however, a torsion spring 82 is present. Torsion spring 82 can vary in cross-section to be a normal round wire or a square wire, which makes more contact with the bottom shaft to increase grip thereon. Further included on bottom shaft or bottom shaft end 73b is a mounting plate 83, on which an electrical contact 84 is connected. One end of the Nitinol 72 is connected to the electrical contact 84. The other end of the Nitinol 72 is connected to the other electrical contact at the other end of the feed tube 7, for instance at post 85 which acts as both an anchor for the Nitinol 72 and the positive or negative terminal since electrical polarity is required (pair of terminal posts mounted to the valve assembly are a means for anchoring and polarizing the Nitinol 72). Upon voltage being applied, the Nitinol 72 contracts, thereby pulling on torsion spring 82, as a result rotating butterfly valve 71. Because Nitinol 72 takes time to relax from its contracted state, the Nitinol 72, as a means for being urged from its contracted state, can be urged by being stretched using a return spring 86 which is preferably mounted with one end to an anchor 87, the other end attached to the Nitinol 72. As an alternative means, the return spring 86 for the Nitinol 72 can be connected to the wrap spring slip clutch or in alternate, directly to a Butterfly shaft side lever or directly to the Nitinol, if a slip clutch is not used. For instance, referencing FIG. 15, the Nitinol can be wrapped directly around the Butterfly valve shaft 73 instead of using a standard type wrap spring clutch. The Nitinol is wrapped around the shaft 73, forms a loop, which is closed off and connected to a solder ring 82b for instance. One end of the return spring 82 is then connected to the solder ring 82b and the other end of the return spring 82 is connected to the anchor 87.

Figure 10:
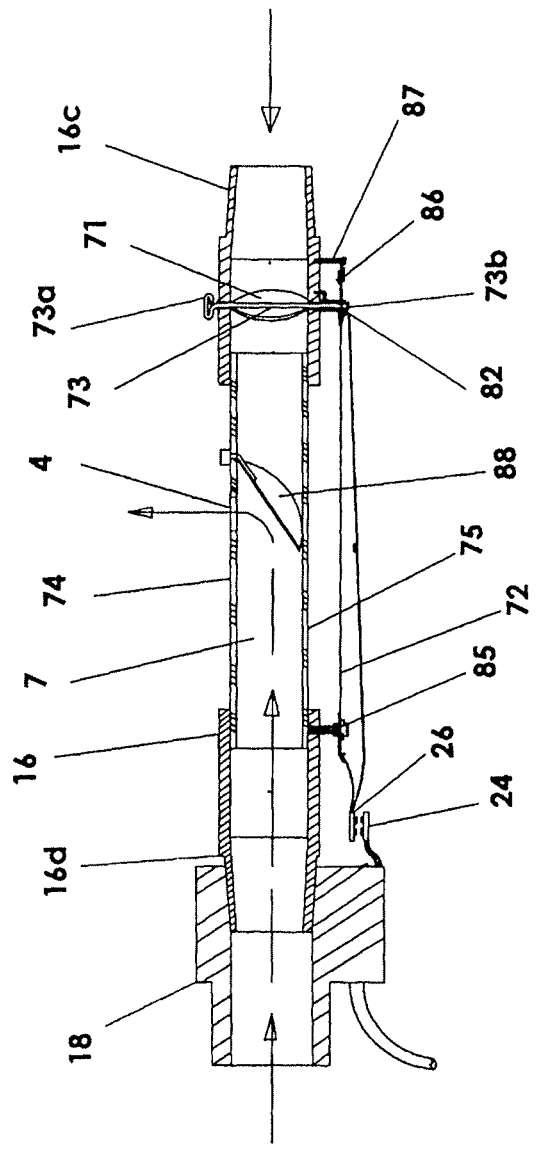
FIG. 10 shows an elevational view in vertical section of the same embodiment of FIG. 9 but in a valve-open position.
Figure 11:
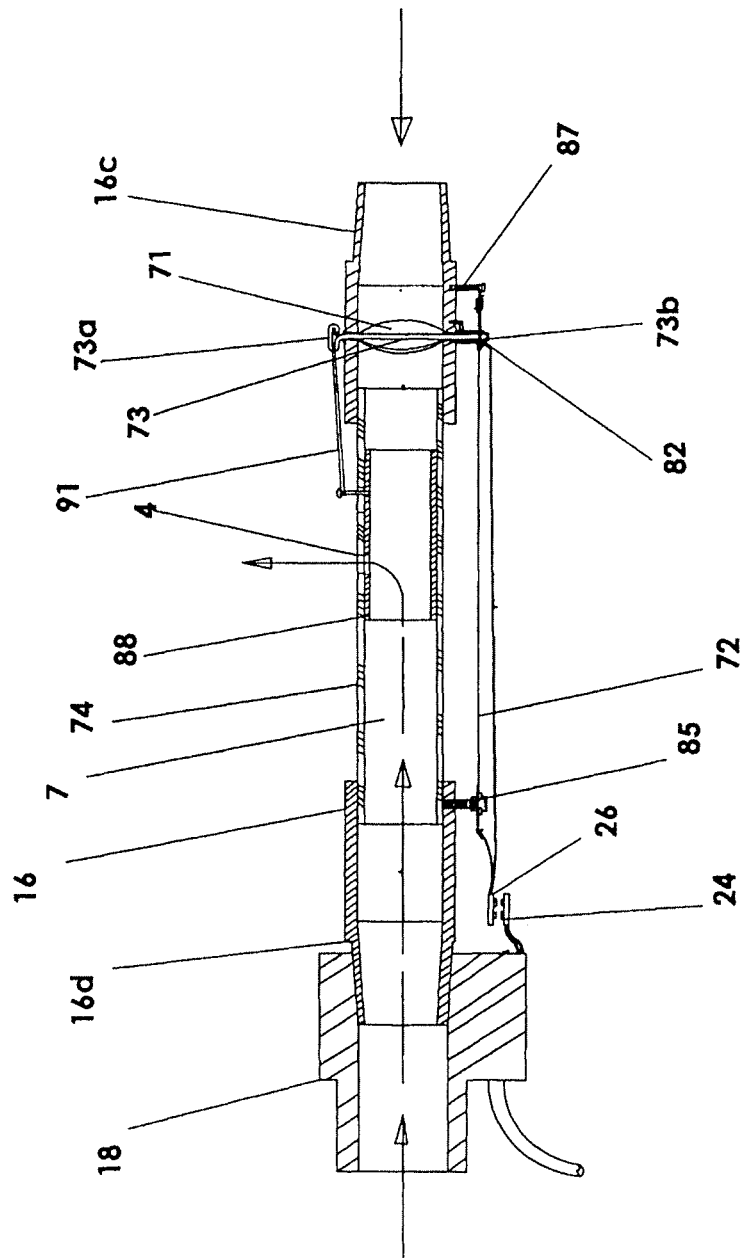
FIG. 11 shows an elevational view in vertical section of a similar embodiment of FIGS. 9 and 10 but wherein a variation of the exhalation valve takes the form of a thin tube section within a tube.
Figure 12:
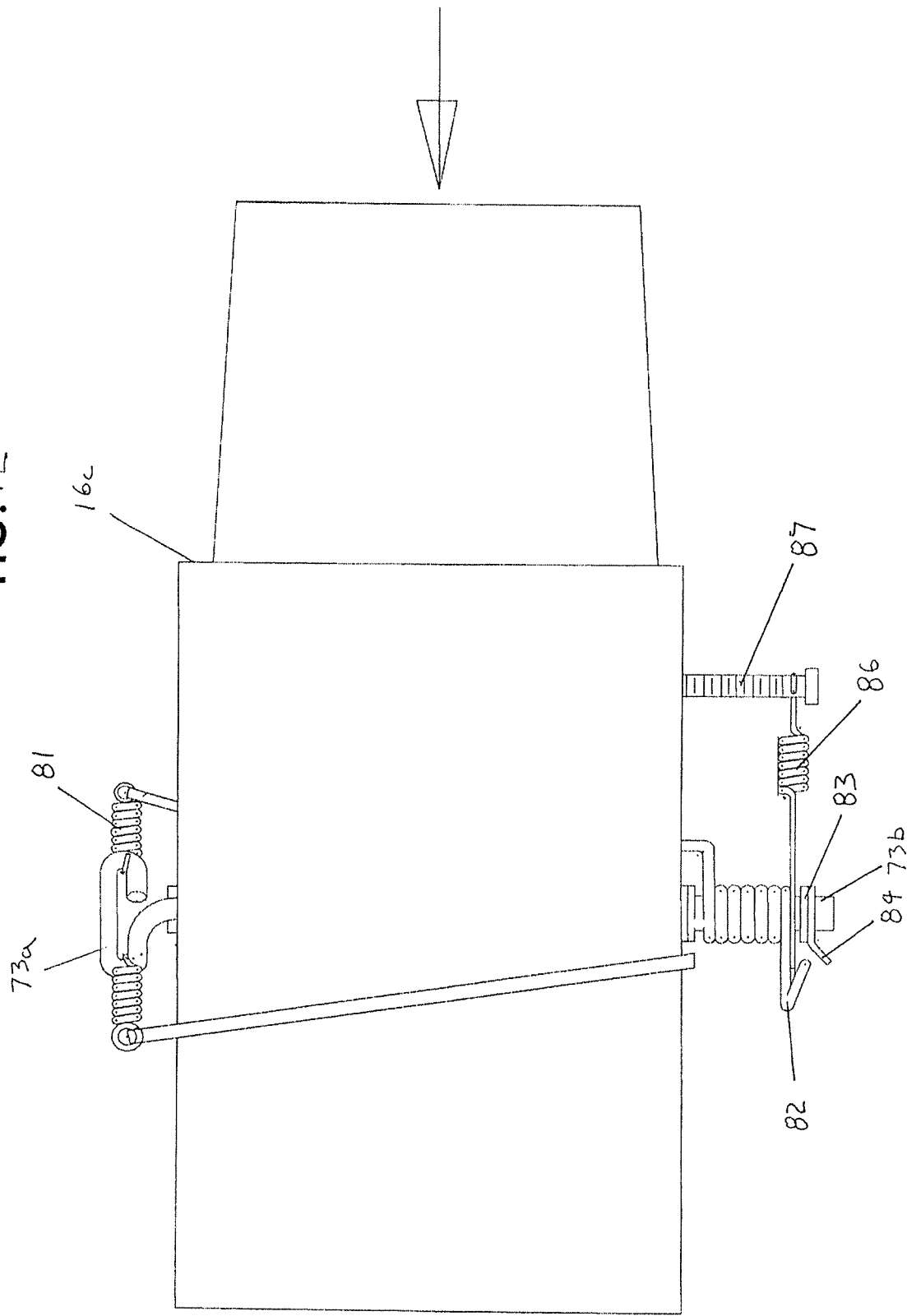
FIG. 12 shows a blown-up elevational view of the slip clutch shown in FIG. 9 used to open and close the valve.
Figure 13:
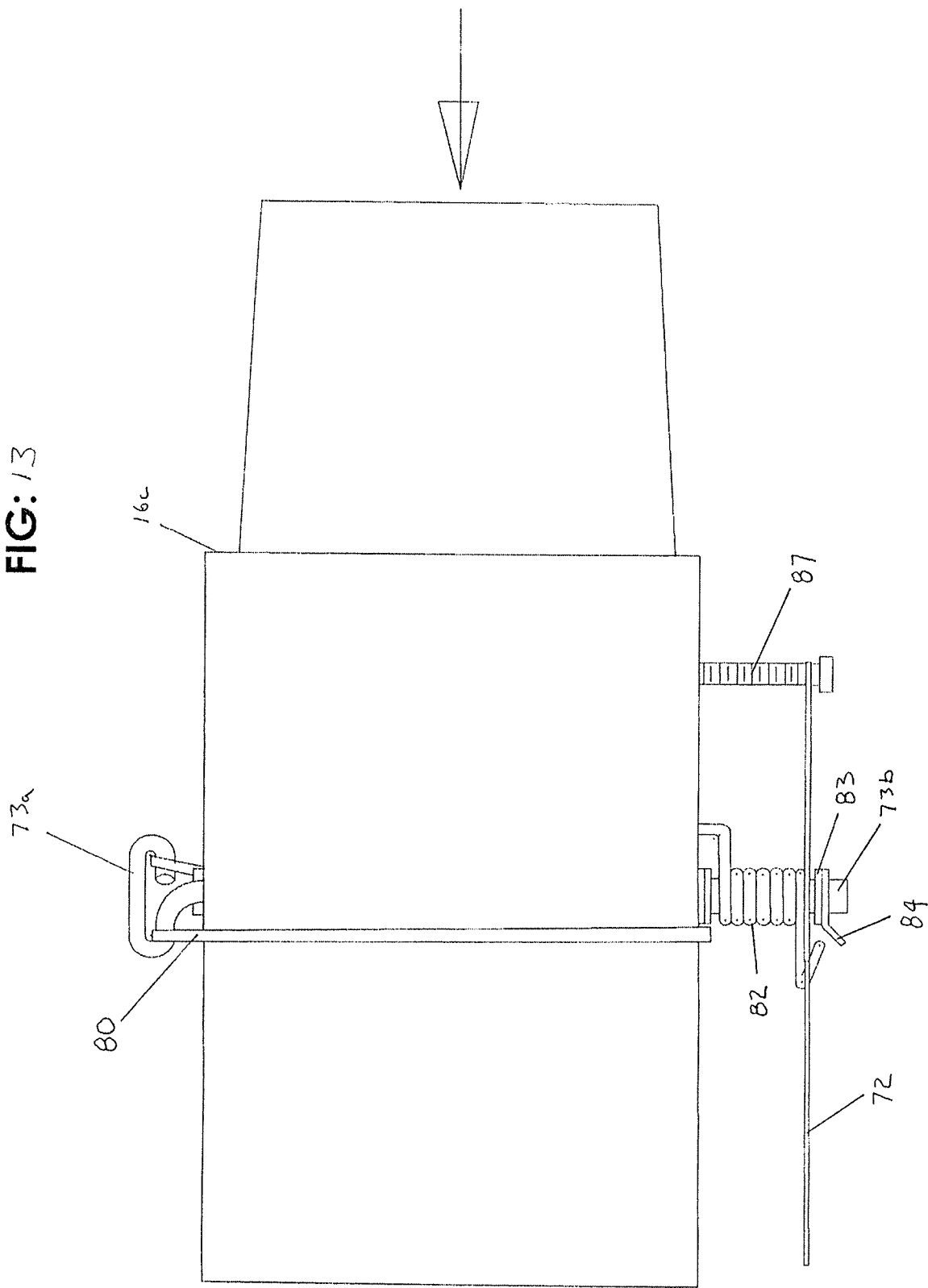
FIG. 13 shows a blown-up elevational view of an alternative embodiment of the slip clutch.
Figure 14:
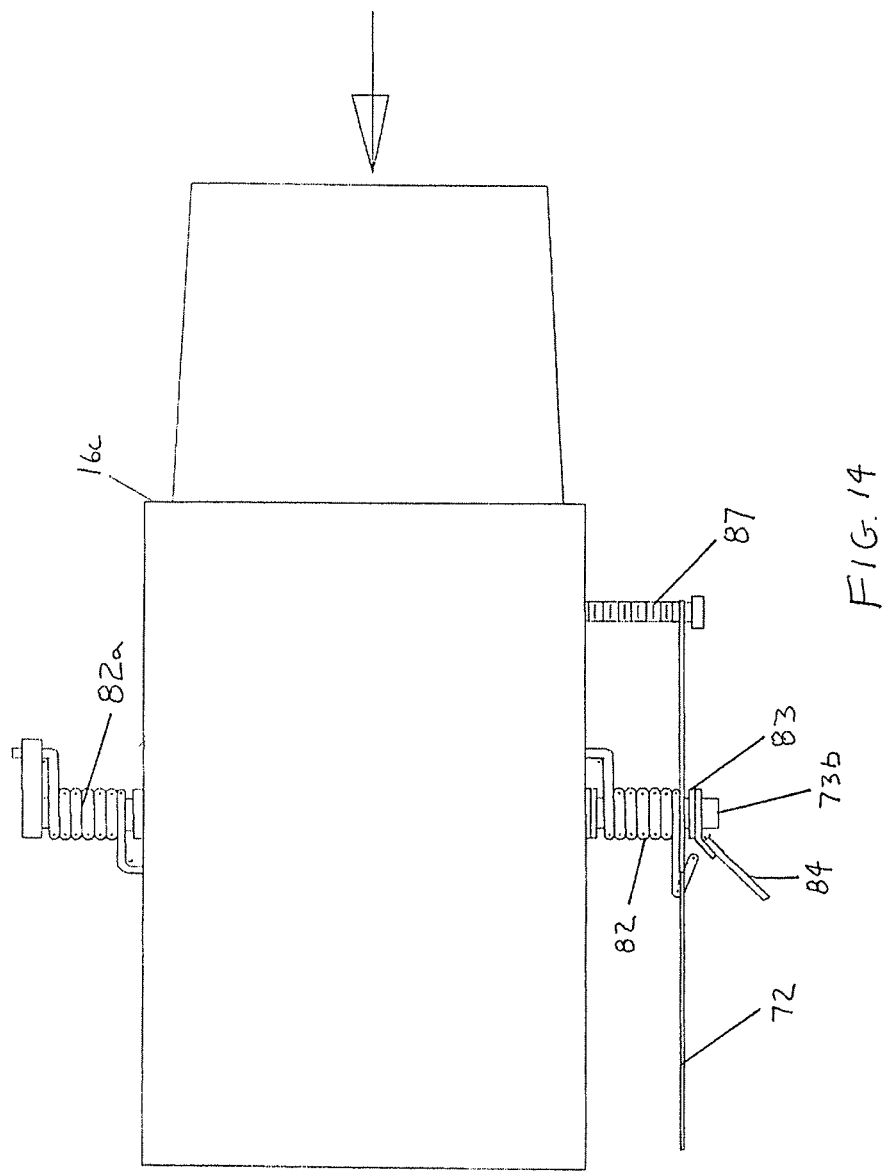
FIG. 14 shows a blown-up elevational view of an even further embodiment of the slip clutch used to open and close the valve.
Figure 15:
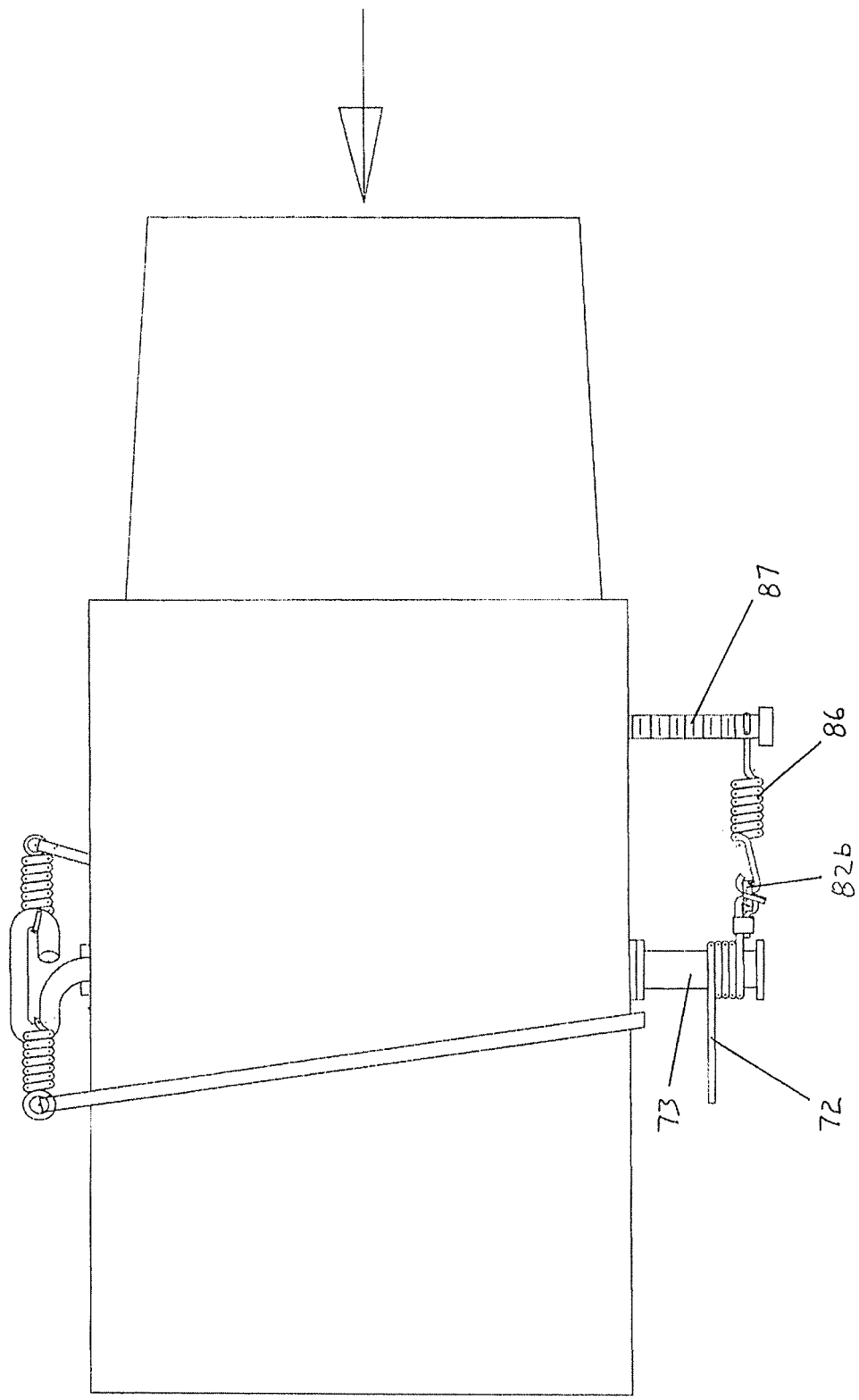
FIG. 15 shows a blown-up elevational view of an embodiment of the Nitinol wire in communication directly with the shaft of the butterfly valve and coupled to a return spring.
Figure 16:
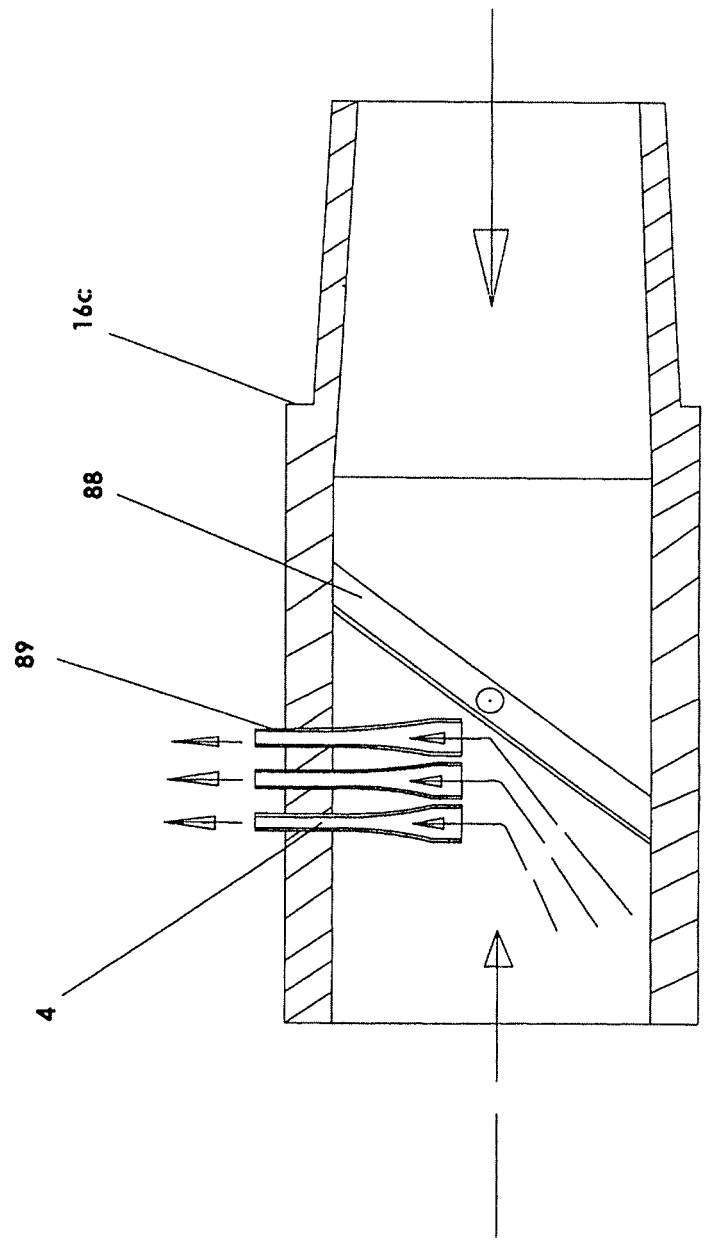
FIG. 16 shows a blown-up elevational view in vertical section of an embodiment similar to FIG. 10 with the valve in an open position but further including, for exhalation, multiple, funnel-shaped vents used to reduce exhalation noise.

The type of exhalation valve 88 covering outlet 4 may vary according to but not limited to the embodiments of FIGS. 10, 11, and 16 and is critical only by its capability to release exhaled breath from the feed tube 7 through outlet 4 defined through top 74 of feed tube 7. Any type of mechanical valve can be used. FIG. 10 shows the exhalation valve 88 in an open-position, attached within interior of feed tube 7. In this embodiment the exhalation valve 88 is a flapper valve hingedly attached to top 74 of feed tube 7. FIG. 11 shows an embodiment of the exhalation valve 88 which takes the form a thin tube section within a larger tube, the larger tube connected to a rigid or flexible member such as a connector band 91 which closes when the butterfly valve 71 opens and which opens for exhalation when the air flow is shut-off. With reference to FIG. 16, one or more funnels 89 disposed across outlet 4 can also be used. Here, the butterfly valve 71, when open, seals off the funnels 89 and thus allows the air to flow thru the tube 7 and switch (valve and air flow shown in dotted line). When the butterfly valve 71 is closed (valve and air flow shown in solid line) air from the CPAP unit is sealed off and the patient exhales thru the funnels 89 (funnel shaped vents), the exact number of which may vary.

In use therefore, upon inhalation, switch 18 (FIG. 1) programmed by controller circuit 12 (FIG. 1) charges the Nitinol 72. The Nitinol 72 immediately contracts to open butterfly valve 71. An exhalation valve 88 at the top of the feed tube 7 closes until the Nitinol 72 stops contracting. The Nitinol then expands and releases and releases the shaft 73 attached to the butterfly valve 71. This shuts off the airflow and opens the exhalation valve 88. The cycle then repeats with each breath.

Figure 17:
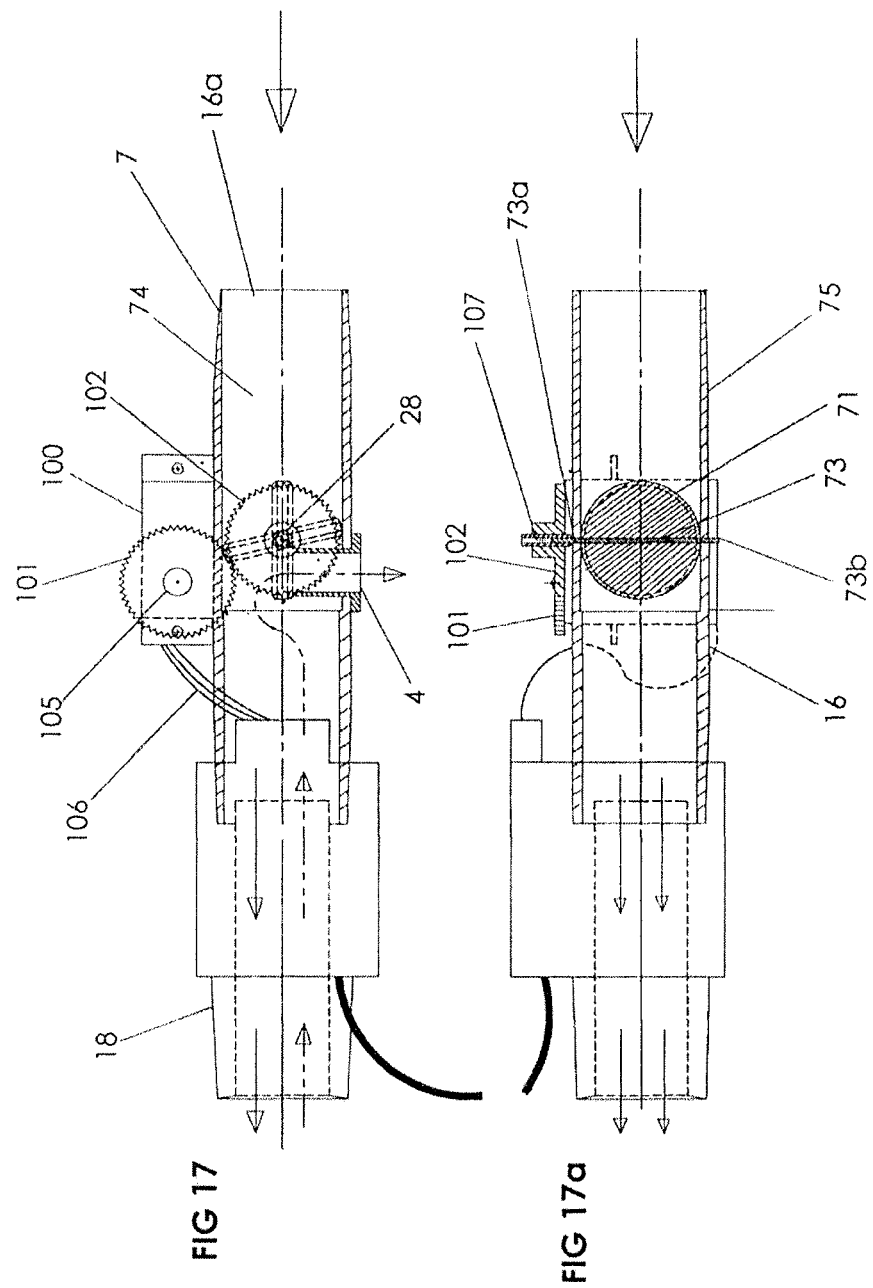
FIG. 17 shows a top view (partially in plan and partially in elevation) of a further embodiment illustrating a valve assembly which includes a servo-operated drive means and butterfly valve.

Referencing now FIGS. 17 and 17a, shown is an embodiment which includes all flow characteristics of the previously-mentioned regulator designs, but in the instant embodiment the motor means includes a servo motor 100. Particularly, herein the valve assembly 16 includes a servo motor 100 signaled by the airflow. Preferably, the servo motor 100 is mounted exterior to the feed tube 7 and can be mounted at various locations along the feed tube 7, shown herein in FIG. 17 mounted to the side. The servo motor 100 is attached by way of power wires 106 and conductors (not shown) to the flow switch/sensor 18, which is mounted on to the feed tube 7. The switch 18 and the valve assembly 16 can be enclosed in any type of protective housing (not shown). The feed tube 7 in this preferred embodiment is a one-piece tube axially aligned, in its entirety, with the inlet 16a. The exhalation outlet 4 (exit tube) is trans-axial, or perpendicular to the feed tube 7 as shown.

A drive means is attached to and powered by the servo motor 100. Drive means can be any combination of one or more drive gears, gear sections (gear fans), lever arms (horns), in conjunction with connecting bar or pulleys with belts. There can be several gears utilized of different sizes and numbers. Shown herein is one or more drive gears, namely a first drive gear 101 and second drive gear 102. First drive gear 101 is mounted on the servo motor 100. The second drive gear 102 is mounted to the top 74 of the feed tube 7 and in engagement (by meshing) with the first drive gear 101. Accordingly, the valve seal 28 within the feed tube is connected to and operable by the drive gears 101, 102, the valve seal 28 adapted to cycle within the feed tube 7 across the exhalation outlet 4, as further described.

Valve seal 28 in this embodiment takes the form of butterfly valve 71. The butterfly valve 71 is attached to a shaft 73 within the feed tube 7. A top shaft end 73a terminates at the top 74 of the feed tube 7, and a bottom shaft end 73b terminates exterior to a bottom 75 of the feed tube 7 to form the shaft 73 perpendicular to the feed tube 7. The second drive gear 102 is then connected to the valve seal 28 by way of a bushing 107 concentrically located through the second drive gear 102 mating therewith and mating with the top shaft end 73a of the butterfly valve 71. As such, the butterfly valve 71 is attached to the shaft 73 and adjacent to the exhalation outlet 4 such that the drive means can cause the butterfly valve 71 to rotate across the exhalation outlet 4. In accordance with the aforementioned, a controller circuit is connected to the servo motor 100 for operating the servo motor 100 incrementally; and, wherein upon activation of both the airflow generator and the controller circuit, pressurized air from the airflow generator continuously enters the feed tube 7 from the inlet 16a but passes out of the feed tube 7 and into the switch 18 (flow sensor) only when the servo motor 100 causes the valve seal 28 to move in relation to the outlet 4 to at least partially block the exhalation outlet 4 such that the pressurized air is converted into a single, repeatable burst exiting the flow sensing switch 18.

In use, as the servo motor shaft 105 rotates back and forth, the gears 101, 102 in turn rotate to open and close the butterfly valve 71, which when in the closed position shuts off the continuous airflow source and allows for exhalation through exhalation outlet 4. When open air flows through the system and the butterfly valve 71 seals against the exhalation outlet 4 (or in alternate outlet funnel) optimum pressure can be maintained. FIG. 17 shows the butterfly valve disc 71 in phantom for both open and closed positions. The exhalation outlet 4 can be of any shape as long as it seals against the butterfly valve disc 71. The butterfly valve disc 71 may contain a softer material sealing layer (not shown) to enhance shutoff. This embodiment as with all configurations may allow adjustment of air flow via adjustment of the air generator. This also may be maintained by leakage around the exhalation outlet 4 or around the butterfly valve disc 71.

Figure 18:
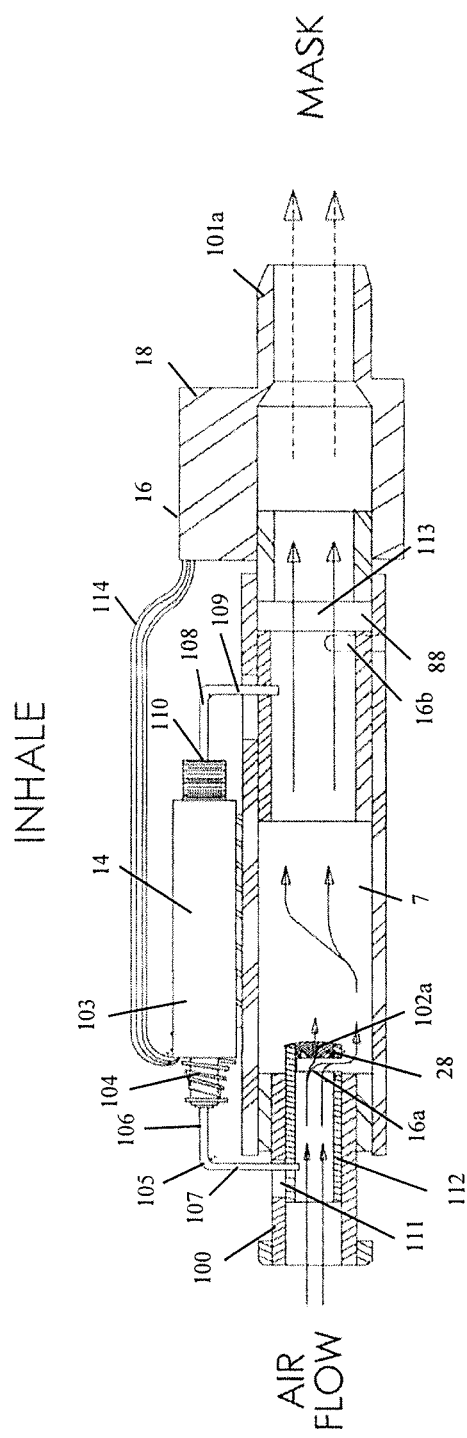
FIG. 18 shows a side view in vertical cross section of a further embodiment illustrating a valve assembly which includes a push-type servo-operated drive means and dual-valve arrangement with the valves operating in unison at inhalation.
Figure 18A:
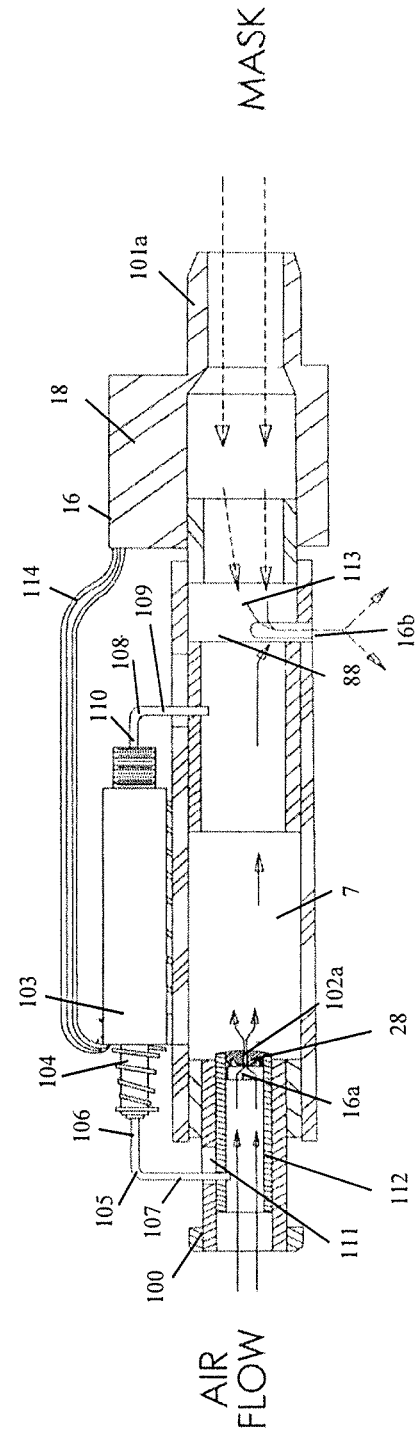
FIG. 18a shows the side view in vertical cross-section of the embodiment of FIG. 18 but with the valves operating at exhalation.

Referencing now FIGS. 18 and 18a, shown is an embodiment which includes all flow characteristics of the previously-mentioned regulator designs, but in the instant embodiment the motor means includes a linear actuator. "Linear actuator" means a solenoid 14 or a Nitinol motor (not shown). "Solenoid" as it relates to this embodiment is any push-type or push-pull type which includes a reciprocating or movable piston 104. In the instant example, shown herein the valve assembly 16 includes a solenoid which is of a push-type solenoid 103 signaled by the airflow. Preferably, the push-type solenoid 103 is mounted exterior to the feed tube 7 and can be mounted at various locations along the feed tube 7, shown herein in FIGS. 18 and 18a mounted to the top. The push-type solenoid 103 is attached by way of wires 114 and conductors (not shown) to the flow switch/sensor 18, which is mounted on to the feed tube 7. The switch 18 and the valve assembly 16 can be enclosed in any type of protective housing (not shown). The feed tube 7 in this preferred embodiment is a concentrically or ring layered-multi piece tube axially aligned, in its entirety, with the inlet 16a. It may also be molded in varying components. The outlet 16b (exit slot) is trans-axial, or perpendicular to the feed tube 7 as shown.

The drive means is attached to and powered by the push-type solenoid 103. The drive means can be any combination of one or more drive rods or linkages, all thread, flexible tubing or rigid tubing. In addition, there can be several drive components utilized of different sizes, shapes, types and numbers. Shown herein with push-type solenoid 103, push-type solenoid 103 includes an axially moving piston 104, having attached thereto a first drive rod 105 and a second drive rod 108. First drive rod 105 is mounted to the solenoid motor piston 104 on the airflow side. The second drive rod 108 is mounted to the piston 104 and to the exhalation valve 88 at the mask side 101a. More particularly, a first drive rod 105 has a first distal end 106 and a first proximal end 107 relative to the location towards the airflow side. The first distal end 106 is connected to the piston 104 on the airflow side 100 with the first proximal end 107 connected to the inhalation valve 102a. A second drive rod 108 has a second distal end 109 and a second proximal end 110, the second proximal end 110 mounted to the piston 104 on the mask side 101a with the second distal end 109 connected to the exhalation valve 88. Preferably, the first proximal end 107 is perpendicular to the first distal end 106, and the second distal end 109 is perpendicular to the second proximal end 110. The first distal end 106 and second proximal end 110 travel parallel to an axis of the feed tube 7. In this manner, exhalation valve 88, in conjunction with the drive rods 105, 108, simultaneously move to open and close the air flow inlet 16a and air flow outlet 16b, as below.

Valve seal 28 in this embodiment takes the form of sliding inhalation valve 102. The sliding inhalation valve 102a partially within the feed tube 7 is attached to the first proximal end 107 of first drive rod 105. First drive rod 105 therefore extends through a tube adapter 111 to terminate at the air flow side 100 from the solenoid piston 104, as above. In accordance with the aforementioned, a controller circuit is connected to the solenoid 103 for operating the solenoid 103 incrementally; and, wherein upon activation of both the airflow generator and the controller circuit, pressurized air from the airflow generator continuously enters the feed tube 7 from the inlet 16a but passes out of the feed tube 7 and into the switch 18 (flow sensor) only when the solenoid 103 causes the inhalation valve 102a to move in relation to the outlet 16b to at least partially block the outlet 16b such that the pressurized air is converted into a single, repeatable burst exiting the flow sensing switch 18.

In use, as the solenoid piston 104 travels back and forth, valves 88, 102a move in unison, which when in the closed position shuts off most if not all of the continuous airflow source and allows for exhalation through exhalation outlet 16b. When open air flows through the system and the sliding exhalation valve 88 seals against the exhalation outlet 16b optimum pressure can be maintained. FIGS. 18 and 18a show the valves 88, 102a in both open and closed positions. The exhalation valve 88 can be of any shape as long as it seals against the outlet 16b. This embodiment as with all configurations may allow adjustment of air flow via adjustment of the air generator.

Figure 19:
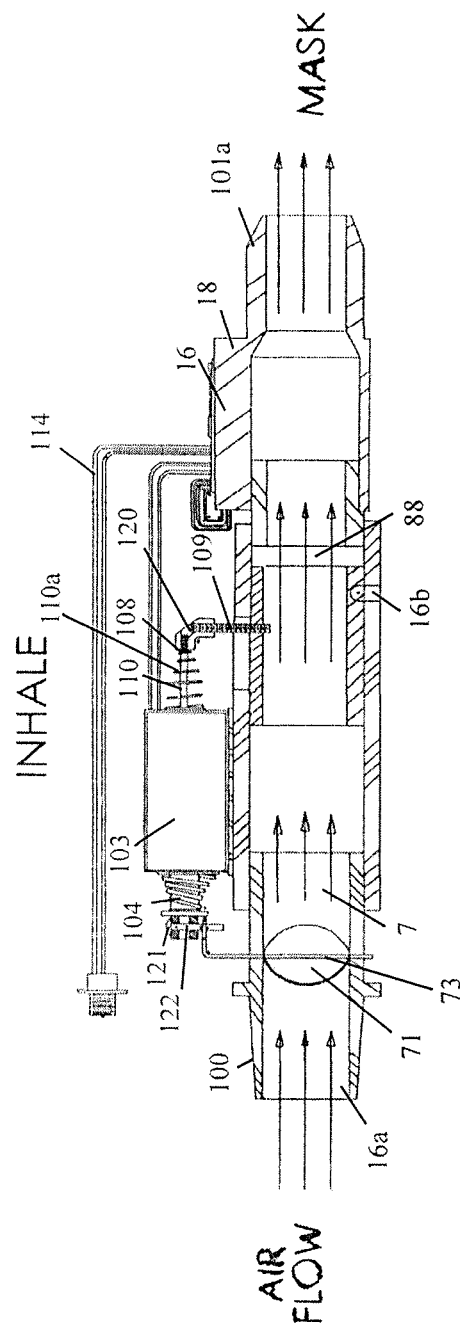
FIG. 19 shows a side view in vertical cross section of a similar embodiment as that shown in FIG. 18 but with a butterfly valve and other linkages.
Figure 19A:
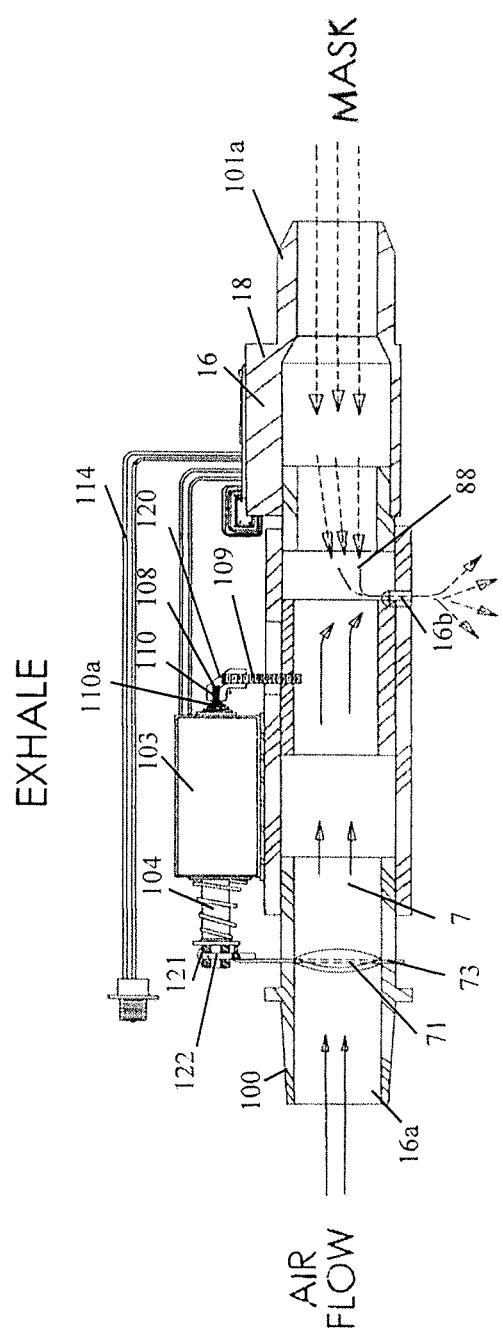
FIG. 19a shows the side view in vertical cross-section of the embodiment of FIG. 19 but with the valves operating at exhalation. Dotted line arrows are shown to depict the direction of patient exhaled breath flow. Solid line arrows mark the air stream flow path of air drawn into the apparatus.

Referencing now FIGS. 19 and 19a, shown is an embodiment which includes all flow characteristics of the embodiment of FIG. 18, but in the instant embodiment the preferred linear actuator is specifically a push-type or push-pull type solenoid 103 which includes a reciprocating or movable piston 104 working in combination with a butterfly valve 71. In the instant example, shown herein the valve assembly 16 includes a solenoid which is of a push-type solenoid 103 signaled by the airflow. Preferably, the push-type solenoid 103 is mounted exterior to the feed tube 7 and can be mounted at various locations along the feed tube 7, shown herein in FIGS. 19 and 19a also mounted to the top. The push-type solenoid 103 is attached by way of wires 114 and conductors (not shown) to the flow switch/sensor 18, which is mounted on to the feed tube 7. The switch 18 and the valve assembly 16 can be enclosed in any type of protective housing (not shown). The feed tube 7 in this preferred embodiment is a concentrically or ring layered-multi piece tube axially aligned, in its entirety, with the inlet 16a. It may also be molded in varying components. The outlet 16b (exit slot) is trans-axial, or perpendicular to the feed tube 7.

The drive means in this embodiment continues to include a combination of one or more drive rods but with additional linkages and tubing. Shown herein with push-type solenoid 103, push-type solenoid 103 includes an axially moving piston 104 working at the airflow side 100. The piston 104 has a piston hole 122 defined therein as shown, distal from the solenoid 103. A pin 121 is loosely disposed vertically within the piston 104, down through the piston hole 122 such that it protrudes down below the distal end of piston 104 as shown and rotates freely. As used herein, "pin" means a needle, screw, rivet, wire or any fastener.

The inhalation valve here is a butterfly valve 71 within the feed tube 7 at the air flow inlet 16a, as was similarly described but with different connection points. Particularly, the butterfly valve 71 includes a valve shaft 73 extending up towards the piston 104. The valve shaft 73 then bends to connect to the pin 121. The valve shaft 73 can connect in a variety of ways, e.g. loop around the pin 121 or pass through a hole (not shown) of the pin 121 so long as the valve shaft 73 slides with the movement of the piston 104. Critical, too, is that the trajectory of the bend of the valve shaft 73 not be exactly axial in relation to the feed tube 7, i.e. if the axis of the feed tube is zero degrees, the bend comes from an angle (within the horizontal plane) as shown, defined herein as off-axis. Accordingly, when the piston 104 and thus the pin 121 are pulled axially towards the mask side 101a, a rotational force is applied to the butterfly valve 71.

The second drive rod 108 is mounted to the piston 104 and to the exhalation valve 88 at the mask side 101a. A second drive rod 108 has a second distal end 109 and a second proximal end 110, the second proximal end 110 mounted to the piston 104 on the mask side 101a with the second distal end 109 connected to the exhalation valve 88. Preferably, the first proximal end 107 is perpendicular to the first distal end 106, and the second distal end 109 is perpendicular to the second proximal end 110. Like the piston 104, the second proximal end 110 travels parallel to an axis of the feed tube 7. A bent tube 120 connects the second distal end 109 to the second proximal end 110. The bent tube 120 can be made of silicon and aids in dampening the pulse or transitional sound of the solenoid 103 and provides for some tolerances between the second proximal end 110 and the second distal end 109 since these are now non-integral (compare FIG. 18). Other dampening or sealing mechanisms can be used throughout any connection point or hole such as O-rings and sleeves. For instance, a sleeve (not shown) can be utilized at outlet 16b. Shown in the instant figures is a dampening spring 110a situated between the bent tube 120 and the solenoid 103 and around the second distal end 109. In addition, although not shown, exhalation valve 88 may include any variety of defined holes or slots.

In accordance with the aforementioned, a controller circuit is connected to the solenoid 103 for operating the solenoid 103 incrementally. The pressurized airflow burst is adjustable by way of the controller circuit 12 which is encoded by way of the programmer 8. In this particular embodiment, the valve assembly 16 will re-calibrate itself to each patient via the first several patient breaths (5-10) each time it is used. Additionally, a forced puff, burst, or rush can be produced incrementally, e.g. every five seconds, when the patient does not breath on his own. These adjustments are in addition to all adjustments, which include, but are not limited to, ramp up time, length of burst, sensitivity of the switch/sensor, timed release of burst or any combination of these settings, should they be required. Accordingly, wherein upon activation of both the airflow generator and the controller circuit, pressurized air from the airflow generator continuously enters the feed tube 7 from the inlet 16a but passes out of the feed tube 7 and into the switch 18 (flow sensor) only when the solenoid 103 causes the butterfly valve 71 to move such that the pressurized air is converted into a single, repeatable burst or rush exiting the flow sensing switch 18. This embodiment as with all configurations may allow adjustment of air flow via adjustment of the air generator.

I claim:

1. An assembly for modifying airflow into a nasopharyngeal airway or trachea of a patient, comprising: a valve assembly adapted to attach to an airflow generator, wherein said airflow generator is a continuous blower of a type producing a constant head of pressurized air, said valve assembly having an airflow side and a mask side, an inlet and an outlet defined between said airflow side and said mask side, and a feed tube, said valve assembly further comprising: a solenoid mounted exterior to said feed tube, said solenoid including a piston working at said airflow side; a butterfly valve within said feed tube at said inlet, said butterfly valve including a valve shaft extending up towards said piston; an exhalation valve within said teed tube at said outlet; a piston hole defined within said piston; a pin loosely disposed vertically within said piston through said piston hole; said valve shaft bent to connect to said pin, wherein a rotational force is applied to said butterfly valve upon axial movement of said piston; a drive rod having a distal end and proximal end, said proximal end mounted to said solenoid on said mask side, said distal end connected to said exhalation valve; a controller circuit connecting to a motor means for operating said solenoid incrementally; and, wherein upon activation of both said airflow generator and said controller circuit, pressurized air from said airflow generator continuously enters said feed tube from said inlet but passes out of said outlet only when said solenoid causes said butterfly valve to move in response to inhalation of said patient and thereby simultaneously move said exhalation valve to at least partially block said outlet such that said pressurized air is converted into a single, repeatable burst.

2. The assembly of claim 1, further comprising a bent tube connecting said distal end to said proximal end.

3. The assembly of claim 2, further comprising a dampening spring situated between said bent tube and said solenoid around said distal end.

4. The assembly of claim 1, wherein said valve shaft is bent off-axis.

5. The assembly of claim 1, wherein said burst is produced every five seconds.

6. The assembly of claim 1, wherein said valve assembly can be calibrated to said patient.

* * * * *